United States Patent [19]

Häbich et al.

[11] Patent Number: 4,841,042
[45] Date of Patent: Jun. 20, 1989

[54] PROCESS FOR THE PREPARATION OF CARBAPENEM INTERMEDIATES

[75] Inventors: Dieter Häbich; Wolfgang Hartwig, both of Wuppertal, Fed. Rep. of Germany

[73] Assignee: Bayer Aktiengesellschaft, Leverkusen, Fed. Rep. of Germany

[21] Appl. No.: 838,237

[22] Filed: Mar. 10, 1986

[30] Foreign Application Priority Data

Mar. 19, 1985 [DE] Fed. Rep. of Germany ....... 3509769

[51] Int. Cl.⁴ ................. C07D 205/08; C07D 401/06; C07F 7/18; C07B 37/04
[52] U.S. Cl. .................................. 540/200; 540/350; 540/364
[58] Field of Search ............................... 540/364, 200

[56] References Cited

U.S. PATENT DOCUMENTS

| 4,312,871 | 1/1982 | Chistenson | 540/200 |
| 4,382,949 | 5/1983 | Afonso | 540/200 |
| 4,539,152 | 9/1985 | Hashinoto | 540/302 |

FOREIGN PATENT DOCUMENTS 0078026  5/1983  European Pat. Off. .

OTHER PUBLICATIONS

Jeffrey J. Org. Chem, 1982, vol. 47, pp. 587–589.
Canadian Journal of Chemistry 1984 vol. 62 pp. 2936–2940.
Seard Report for EP 102,971.

Primary Examiner—Mark L. Berch
Attorney, Agent, or Firm—Sprung Horn Kramer & Woods

[57] ABSTRACT

A process for the preparation of a 4-[3-carboxy-3-diazo-2-oxopropyl]azetidin-2-one of the formula

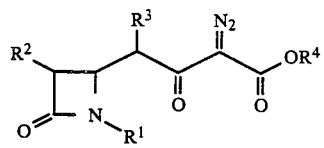

comprising reacting a 4-acetoxy-2-azetininone of the formula

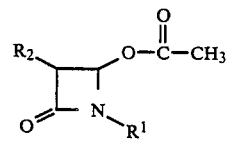

with a compound of the formula

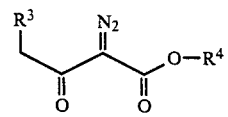

in an inert solvent, in the presence of a base and of a silylating agent, in a one-pot process.

Many of the products are new. The products are useful in the synthesis of carbapenem antibiotics.

4 Claims, No Drawings

PROCESS FOR THE PREPARATION OF CARBAPENEM INTERMEDIATES

The invention relates to a new process for the preparation of 4-[3-carboxy-3-diazo-2-oxopropyl]azetidin-2-ones which are important intermediates for the synthesis of carbapenem antibiotics and some of which are known.

It is known that 4-acetoxyazetidinones react with trimethylsilyl enol ethers in the presence of Lewis acids to give the corresponding C-C-linked 4-[3-carboxy-3-diazo-2-oxopropyl]azetidin-2-ones (compare European Patent Application No. 78026; J. D. Buynak et al., J. Chem. Soc., Chem. Commun. 1984, 948). This entails the separate and very elaborate preparation of the trimethylsilyl enol ethers used in each case. Since to date in their preparation organometallic bases, such as n-butyllithium or lithium diisopropylamide, have been used, these methods of preparation cannot be combined with the most important and most frequently used carbapenem ester protective group, the 4-nitrobenzyl ester. In addition, to date only zinc (II) halides have been used as Lewis acids in the linkage of diazoenol ethers. Heterogeneous reactions of this type in some cases require elevated reaction temperatures and long reaction times (compare European Patent Application No. 78,026; J. D. Buynak, J. Chem. Soc., Chem. Commun. 1984, 948; P. J. Reider et al., Tetrahedron Lett. 1982, 379), which, as is well known, can have very disadvantageous effects because of the sensitivity of the products.

In addition, it is known that for the reaction to succeed in most cases preceding and separate incorporation of a N-protective group is necessary (compare M. Shiozaki et al., J. Org. Chem. 39, 2399 (1983); M. Shiozaki et al., Tetrahedron 40, 1795 (1984) and Tetrahedron Lett. 1984, 2793; A. G. M. Barrett, J. Org. Chem. 49, 1679 (1984)).

It is also known that direct reaction of 4-acetoxyazetidinones with lithium enolates provides poor yields and can likewise only be carried out with esters which are insensitive to organometallic compounds (compare T. Kametani et al., Heterocycles 14, 1967 (1980); T. Kametani et al., J. Chem. Soc., Perkin I 1981, 2228).

It has now been found that 4-[3-carboxy-3-diazo-2-oxopropyl]azetidin-2-ones of the general formula I

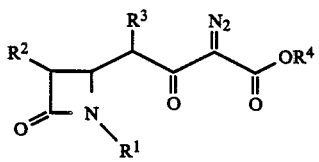

in which
R¹ represents hydrogen or represents an amino protective group,
R² represents hydrogen, represents optionally substituted alkyl, represents optionally substituted aryl, represents optionally substituted heterocyclyl, represents cyano, azido or halogen, or represents NHR¹, R¹ having the abovementioned meaning,
R³ represents hydrogen, represents optionally substituted alkyl, represents optionally substituted aryl, represents optionally substituted heterocyclyl, represents halogen, cyano, cyanato, azido, nitro or =N—phenyl,
represents —COR⁵, —CO₂R⁵, —CO—NR⁵R⁶, —C(=NR⁵)NR⁵R⁶, —CSNR⁵R⁶
represents —NR⁵R⁶, —NR⁵—COR⁶, —NR⁵—CO₂R⁷, —NR°—CR⁵(=NR⁶), —NR⁶—CO—NR⁵R⁶, —NR⁵—CS—NR⁵R⁶, —NR⁵—C(=NR⁶)—NR⁵R⁶, —NR⁵—SO₂R⁷,
represents —OR⁵, —OCOR⁵, —OCO—NR⁵R⁶, —OSO₂R⁷, —OSO₃R⁵, —OPO(OR⁵)OR⁶, or
represents —SR⁵, —S(O)ₙR⁷ n being 1 or 2, —SCOR⁵, —SO₂OR⁵, —SO₂NR⁵R⁶, —SCN, —SCONHR⁵,
or represents —PX(OR⁵)OR⁶, —PX(NR⁵R⁶)₂, —PX(OR⁵)NR⁵R⁶
in which in each case
R⁵ and R⁶ are identical or different and represent hydrogen, represent optionally substituted alkyl, represent optionally substituted aryl, represent optionally substituted heterocyclyl, or optionally represent a protective group for hydroxyl, mercapto, amino or carboxyl,
R⁷ has the same meaning as R⁵ and R⁶ but does not represent hydrogen or a protective group, and X represents oxygen or sulphur, and
R⁴ represents a protective group for carboxyl or represents an ester radical which can be cleaved in vivo,
are obtained by reacting 4-acetoxy-2-azetidinones of the general formula II

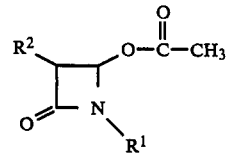

in which
R¹ and R² have the abovementioned meaning, with compounds of the general formula III

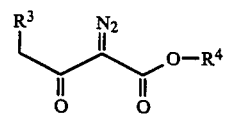

in which
R³ and R⁴ have the abovementioned meaning, in an inert solvent and in the presence of a base and a silylating agent, in a one-pot process.

It may be designated extremely surprising that the compound of the formula I is obtained in good yields by the process according to the invention. It was not to be expected from the state of the art that the compound of the general formula I can be prepared by the one-pot process, according to the invention, in homogeneous solution.

Apart from the simplicity of the procedure and the mild conditions, the process according to the invention has the advantage that there is no need for the separate, elaborate preparation of the precursors which are sensitive to hydrolysis. In addition, the new process also allows the use of the important nitrobenzyl protective groups. The silylating agent which is used simultaneously acts as a catalyst, which makes it unnecessary to use other Lewis acids. Furthermore, the process can also be used for the preparation of those compounds I in which the radical $R^3$ is a substituent bonded via a heteroatom (for example —OCH₃).

The azetidinones which can be prepared by the process according to the invention are generally defined by the formula (I). In this formula $R^1$ preferably represents hydrogen or preferably represents an amino protective group, $R^2$ preferably represents hydrogen, preferably represents fluorine, chlorine, bromine or azido, preferably represents phenyl, preferably represents $NHR^1$, $R^1$ having the abovementioned meaning, preferably represents a radical of the formula

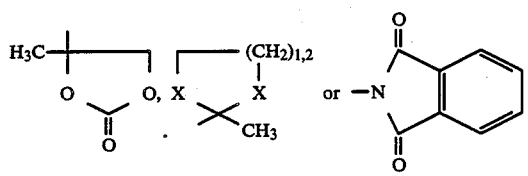

X denoting sulphur or oxygen, or
preferably represents straight-chain, branched or cyclic, saturated or unsaturated, alkyl having up to 6 C atoms, which is optionally substituted by fluorine, chlorine or the group $OR^8$, $R^8$ representing hydrogen, or
preferably representing trimethylsilyl, triethylsilyl, triisopropylsilyl, tert.-butyldimethylsilyl, triphenylsilyl or trimethylsilylethoxycarbonyl, preferably represents benzyl, benzyloxycarbonyl, 2- or 4-nitrobenzyl, 2- or 4-nitrobenzyloxycarbonyl, tert.-butyloxycarbonyl, allyloxycarbonyl, 4-methoxybenzyl, 4-methoxybenzyloxycarbonyl, or preferably represents formyl, acetyl, trichloroacetyl, trichloroethoxycarbonyl, 2,4-dimethoxybenzyloxycarbonyl, methoxymethyl, methylthiomethyl, methoxyethoxymethyl, [2-(trimethylsilyl)ethoxy]methyl, 2-(methylthiomethoxy)ethoxycarbonyl, tetrahydropyranyl or benzoyl;

$R^3$ preferably represents hydrogen, preferably represents phenyl which is optionally substituted by chlorine, nitro, methyl, methoxy, methylthio, trifluoromethyl or by (optionally protected) hydroxyl, preferably represents fluorine, chlorine, bromine, cyano, cyanato or azido, preferably represents thienyl, furyl, imidazolyl, thiazolyl, thiadiazolyl, triazolyl, tetrazolyl, pyridyl, piperazinyl or pyrimidyl, each of which is optionally substituted by methyl, amino (optionally protected), fluorine, chlorine, trifluoromethyl or hydroxyl, preferably represents S-heterocyclyl, heterocyclyl having the meaning of triazolyl, tetrazolyl, thiadiazolyl, furyl, thienyl, pyridyl or pyrimidyl each of which is optionally substituted by methyl, amino, hydroxyl or acetylamino, preferably represents —COR⁵, —CO₂R⁵, —CONHR⁵, amidino, preferably represents —NR⁵R⁶, ureido, guanidino, preferably represents —OR⁵, —OCOR⁵, —O-SO₂R⁷, —OPO(OR⁵)₂, preferably represents —SR⁵, —S(O)ₙR⁷ with n=1 or 2, —SCOR⁵, —S-CONHR⁵, —SO₂OR⁵, —SO₂NHR⁵, —SCN or preferably represents —PO(OR⁵)₂, —PO(NR⁵R⁶)₂, where in each case $R^5$ and $R^6$ are identical or different and represent hydrogen, represent straight-chain, branched or cyclic, saturated or unsaturated, alkyl having up to 6 C atoms, which is optionally substituted by phenyl or one or more fluorine, represents phenyl which is optionally substituted by nitro or methoxy, represents furyl, thienyl or pyridyl, or represents a protective group for hydroxyl, mercapto, amino or carboxyl, and $R^7$ has the same meaning as $R^5$ and $R^6$, but does not represent hydrogen or a protective group, or preferably represents straight-chain, branched or cyclic, saturated or unsaturated, alkyl having up to 6 C atoms, which is optionally substituted by phenyl, fluorine, chlorine, furyl, thienyl, pyridyl, imidazolyl, triazolyl, tetrazolyl, thiadiazolyl or a radical of the formula

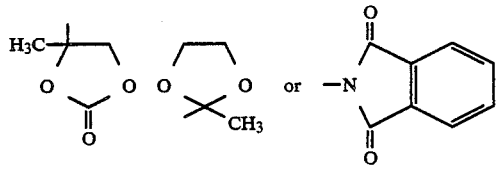

or by —CO₂R⁵, —CONHR⁵, cyano, amidino, —NHR⁵, —NHCOCH₃, guanidino, azido, —OR⁵, —OCOR⁵, —OSO₂R⁷, —OPO(OR⁵)₂, —SR⁵, —SO₂R⁷, —SCOR⁵, —SO₂NHR⁵, —PO(OR⁵)₂, —PO(NR⁵R⁶)₂, where R⁵, R⁶ and R⁷ have the abovementioned meaning, and $R^4$ preferably represents a carboxyl protective group or an ester radical which can be cleaved in vivo.

The one-pot process according to the invention for the preparation of compounds of the general formula I comprises several individual reaction steps.

If the starting material used is:

(a) (3R,4R)-4-Acetoxy-3-[1(R)-1-tert.-butyldimethylsilyloxyethyl]azetidin-2-one ($R^1$ in II=H) and allyl 2-diazo-3-oxo-pentanoate or (b) (3R,4R)-4-acetoxy-3-[1(R)-1-tert.-butyldimethylsilyloxyethyl]-1-(4-methoxyphenyl)azetidin-2-one ($R^1$ in II=H) and 4-nitrobenzyl 2-diazo-3-oxobutanoate, then the course of the reaction can be illustrated by the diagrams which follow:

(a)
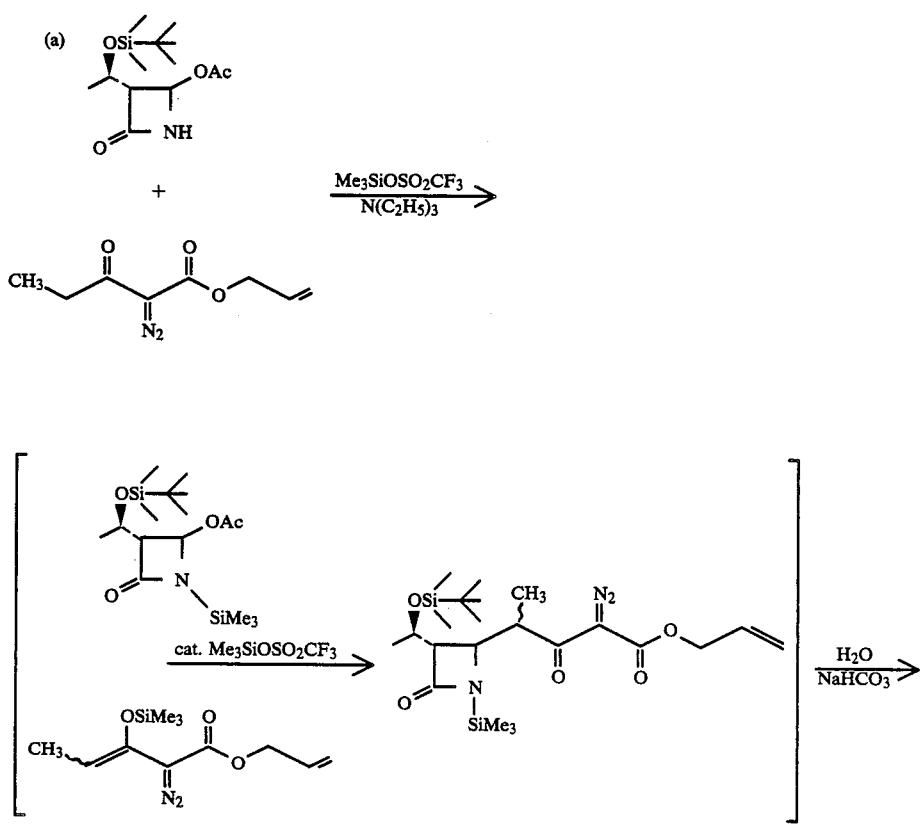
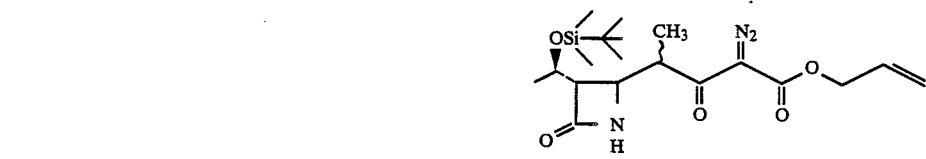
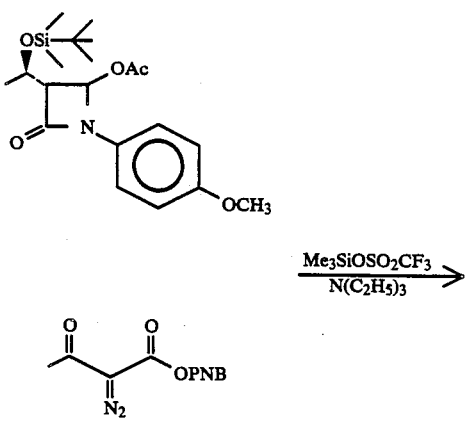

-continued

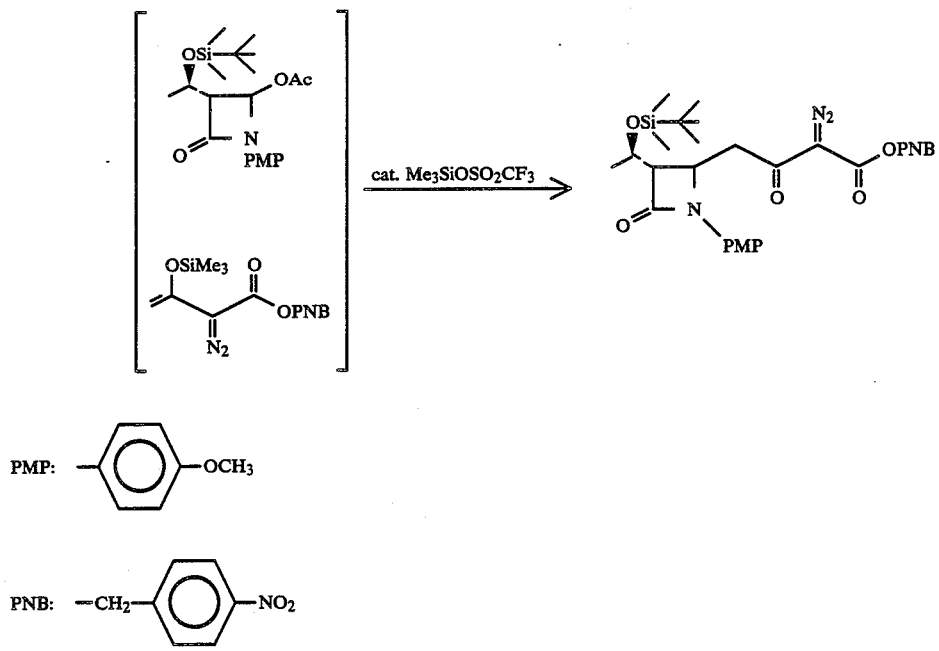

PMP: —⟨C₆H₄⟩—OCH₃

PNB: —CH₂—⟨C₆H₄⟩—NO₂

In the compounds of the general formula I, II or III, where R², R³, R⁵, R⁶ and R⁷ denote optionally substituted alkyl they represent straight-chain, branched or cyclic, saturated or unsaturated alkyl having up to 10 C atoms, preferably up to 6 C atoms. Suitable substituents in this context are:

(a) phenyl which in turn can be substituted several times, preferably up to twice, by methyl, methoxy, methylthio, trifluoromethyl, trifluoromethoxy, trifluoromethylthio, nitro, cyano, or hydroxyl, mercapto or amino each of which is optionally protected, dimethylamino, caramoyl, amidino, sulpho, sulphamoyl or halogen, preferably fluorine, chlorine or bromine, (b) saturated or unsaturated 5–6-membered, optionally fused together, heterocyclyl having 1–4 identical or different heteroatoms from the group comprising O, S or N, preferably thienyl, furyl, pyrrolyl, imidazolyl, pyrazolyl, isothiazolyl, thiazolyl, oxazolyl, isoxazolyl, thiazolyl, tetrazolyl, thiadiazolyl, pyridyl, pyrazinyl, pyrimidyl, pyridazinyl, indolyl, quinolyl, isoquinolyl, quinoxalyl, quinazolyl, purinyl, pteridinyl, pyrrolidinyl, piperidinyl, piperazinyl, morpholinyl, thiomorpholinyl or a radical of the formula

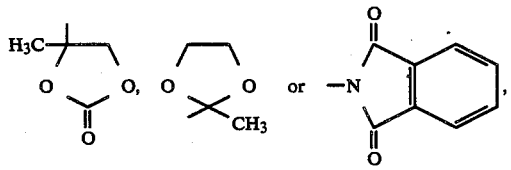

it being possible for the heterocycles in turn to carry the same substituents as already indicated for phenyl, (c) halogen, preferably fluorine, chlorine or bromine, (d) —COR⁹, —CO₂R⁹, —CO—NR⁹R¹⁰, —C(=NR¹⁰)NR⁹R¹⁰, —CN, (e) —NR⁹R¹⁰, —NR⁹—COR¹⁰, —N(COR⁹)(COR¹⁰), —NR⁹CO₂R¹¹, —NR¹⁰—CR⁹(=NR¹⁰), —NR¹⁰—CO—NR⁹R¹⁰, —NR⁹—C(=NR¹⁰)—NR⁹R¹⁰, —NR⁹—SO₂R¹¹, —N₃, (f) —OR⁹, —OCOR⁹, —OCO—NR⁹R¹⁰, —OSO₂R¹¹, —OSO₃R⁹, —OPO(OR⁹)OR¹⁰, (g) —SR⁹, —S(O)ₙR¹¹, n being 1 or 2, —SCOR¹¹, —SO₂OR⁹, —SO₂NR⁹R¹⁰, or (h) —PX(OR⁹)OR¹⁰, —PX(NR⁹R¹⁰)₂, —PX(OR⁹)NR⁹R¹⁰, where in each case R⁹ and R¹⁰ are identical or different and represent hydrogen, represent straight-chain, branched or cyclic, saturated or unsaturated alkyl up to C₁₀, preferably up to C₆, represent phenyl or benzyl, represent heterocyclyl or heterocyclylmethyl, heterocyclyl having the meaning indicated under (b), or optionally represent a protective group for hydroxyl, mercapto, amino or carboxyl, R¹¹ has the same meaning as R⁹ and R¹⁰ but does not represent hydrogen or a protective group, and X represents oxygen or sulphur.

Where R², R³, R⁵, R⁶ and R⁷ denote optionally substituted aryl, they preferably represent phenyl which can be substituted preferably once or twice, and optionally three times, by C₁–C₄-alkyl (preferably methyl or ethyl), C₁–C₄-alkoxy (preferably methoxy), C₁–C₄-alkylthio (preferably methylthio), trifluoromethyl, trifluoromethoxy, trifluoromethylthio, halogen (preferably fluorine, chlorine or bromine), cyano, nitro, azido, dimethylamino, amino, hydroxyl, mercapto (each of which is optionally protected), sulpho, sulphamoyl, acetoxy or carbamoyl.

Where R², R³, R⁵, R⁶ and R⁷ denote optionally substituted heterocyclyl, they preferably represent saturated or unsaturated, 5–6-membered, optionally fused together, heterocyclyl having 1–4 identical or different heteroatoms from the group comprising O, S and N, and particularly preferably represent thienyl, furyl, pyrrolyl, imidazolyl, pyrazolyl, isothiazolyl, thiazolyl, tetrazolyl, thiadiazolyl, pyridyl, pyrazinyl, pyrimidyl, pyridazinyl, indolyl, quinolyl, isoquinolyl, quinoxalyl, pyrrolidinyl, piperidinyl, piperazinyl, benzothiazolyl, benzimidazolyl, purinyl, pteridinyl, morpholinyl, thiomorpholinyl or a radical of the formula

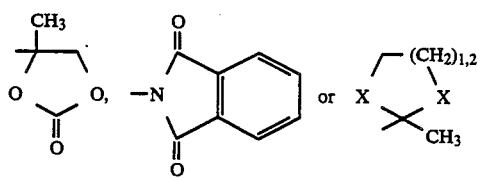

the substituents of heterocyclyl being those already indicated for aryl, and X represents sulphur or oxygen.

In $R^2$, $R^3$, $R^5$, $R^6$ and $R^7$ halogen preferably represents fluorine, chlorine or bromine.

When $R^1$ is an amino protective group then it is preferably one which is customary in β-lactam chemistry. Examples which may be mentioned as particularly preferred are vinyl, allyl, tert.-butyloxycarbonyl, benzyl, benzyloxycarbonyl, 2-nitrobenzyl or 4-nitrobenzyl, 2-nitorbenzyloxycarbonyl or 4-nitrobenzyloxycarbonyl, 4-methoxyphenyl, formyl, benzoyl, acetyl, chloroacetyl, trichloroacetyl, trifluoroacetyl, methyloxycarbonyl, allyloxycarbonyl, trimethylsilyl, triethylsilyl or triphenylsilyl, tert.-butyldimethylsilyl, 2,4-dimethoxybenzyl, 2,4-dimethoxybenzyloxycarbonyl, 4-methoxybenzyl, 4-methoxymethyloxyphenyl, bis(4-methoxyphenyl)methyl, tert.-butoxycarbonylmethyl, allyloxycarbonylmethyl, methoxymethyl, methylthiomethyl, methoxyethoxymethyl, [2-(trimethylsilyl)ethoxy]-methyl, 2-(methylthiomethoxy)ethoxycarbonyl or tetrahydropyranyl.

The terms aminoprotective group and protective groups of hydroxyl and mercapto in the radicals $R^2$, $R^3$ and $R^5$-$R^{11}$ also have the same meaning.

Where $R^4$ and $R^5$, $R^6$, $R^9$ and $R^{10}$ denote a carboxyl protective group they represent the protective groups customary in β-lactam chemistry. Groups which are easily eliminated may be mentioned as preferred, such as methyl, ethyl, tert.-butyl, decyl, 2-chloroethyl, 2,2,2-trichloroethyl, cyanoethyl, diphenylmethyl and triphenylmethyl, acetoxymethyl, allyl, benzyl, 4-methoxyphenyl, 4-nitrobenzyl, 2-nitrobenzyl, 2,4-dimethoxybenzyl, trimethylsilylethyl, dimethyl-tert.-butylsilylethyl, trimethylsilyl, dimethyl-tert.-butylsilyl, acetonyl, 1-phenoxyethyl or 2-methyl-2-propenyl.

The term carboxyl protective group in the radicals $R^2$, $R^3$, $R^5$, $R^6$, $R^9$ and $R^{10}$ has the same meaning.

Where $R^4$ represents an ester radical which can be easily cleaved in vivo, this means pharmaceutically tolerated ester radicals which are easily hydrolyzed in vivo to give free carboxyl groups ($R^4$=H).

Ester radicals $R^4$ of this type are well known in the area of penicillins. In most cases, they improve the absorption properties of the β-lactam compound. In addition, the nature of $R^4$ should be such that it confers on a compound of the formula (I) pharmaceutically acceptable properties and, on cleavage in vivo, releases pharmaceutically acceptable fragments. Examples of groups $R^4$ of this type can be found in German Offenlegungsschrift No. 2,517,316. Preferred ester groups $R^4$ are those of following formulae

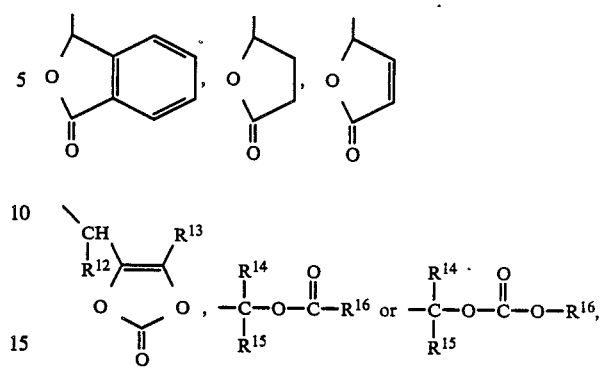

in which
$R^{12}$ and $R^{13}$ are identical or different and represent hydrogen, represent phenyl, or represent $C_1$-$C_4$-alkyl, preferably methyl,
$R^{14}$ and $R^{15}$ are identical or different and represent hydrogen or represent $C_1$-$C_4$-alkyl, preferably methyl, and
$R^{16}$ represents $C_1$-$C_6$-alkyl, preferably $C_1$-$C_4$-alkyl.

Some of the compounds of the general formula I are already known but have been prepared by different processes [compare European Patent Application No. 78,026; J. O. Buynak et al., J. Chem. Soc., Chem. Commun. 1984, 948; U.S. Pat. Nos. 4,444,685 and 4,400,323; D. H. Shih et al., Heterocycles 21, 29 (1984)].

New, and thus the invention likewise relates to them, are compounds of the formula I in which
$R^1$ represents hydrogen or represents an amino protective group,
$R^2$ represents hydrogen, represents halogen, represents azido or phenyl, represents $NHR^1$, $R^1$ having the abovementioned meaning, represents a radical of the formula

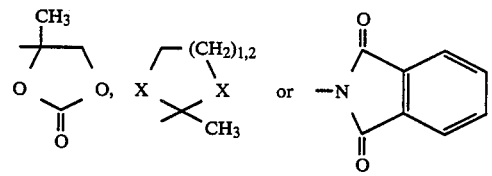

X denoting sulphur or oxygen, or represents straight-chain, branched or cyclic, saturated or unsaturated alkyl (up to $C_6$), which is optionally substituted by fluorine, chlorine or the group O—$R^8$,
$R^8$ representing hydrogen, representing trimethylsilyl, triethylsilyl, triisopropylsilyl, tert.-butyldimethylsilyl, triphenylsilyl, trimethylsilylethoxycarbonyl, representing benzyl, benzyloxycarbonyl, 2- or 4-nitrobenzyl, 2- or 4-nitrobenzyloxycarbonyl, tert.-butyloxycarbonyl, allyloxycarbonyl, 4-methoxybenzyl, 4-methoxybenzyloxycarbonyl, or representing formyl, acetyl, trichloroacetyl, trichloroethoxycarbonyl, 2,4-dimethoxybenzyloxycarbonyl, methoxymethyl, methylthiomethyl, methoxyethoxymethyl, [2-(trimethylsilyl)ethoxy]-methyl, 2-(methylthiomethoxy)ethoxycarbonyl, tetrahydropyranyl or benzoyl,
$R^3$ represents aryl ($C_6$-$C_{10}$) which is optionally substituted by chlorine, nitro, methyl, methoxy, methylthio, trifluoromethyl or (optionally protected)

hydroxyl, or represents halogen, cyano, azido, cyanato, trifluoromethyl or nitro, represents —COR$^{18}$, —CONR$^{18}$R$^{19}$, —CSNR$^{18}$R$^{19}$, or represents allyloxycarbonyl or 4-nitrobenzyloxycarbonyl, represents —NR$^{19}$R$^{18}$, ureido, guanidino, amidino, —NR$^{18}$SO$_2$R$^{20}$, represents —OSO$_2$R$^{20}$, —OSO$_3$R$^{18}$ or —OPO(OR$^{19}$)OR$^{18}$, represents —SR$^{18}$, —S(O)$_n$R$^{20}$ with n=1 or 2, —SCOR$^{18}$, —SCONHR$^{18}$, —SO$_2$OR$^{18}$, —SO$_2$NR$^{19}$R$^{18}$, —SCN, or represents —S-heterocyclyl, heterocyclyl having the meaning of triazolyl, tetrazolyl or thiadiazolyl, each of which is optionally substituted by methyl, amino, hydroxyl or acetylamino, or of furyl, thienyl, pyridyl or pyrimidyl, represents —PO(OR$^{19}$)OR$^{18}$ or represents

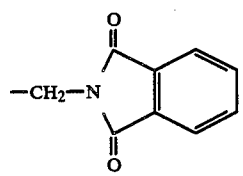

or benzyl,

R$^{18}$ and R$^{19}$ being identical or different and representing hydrogen, representing straight-chain or branched alkyl (up to C$_6$), representing phenyl or benzyl (phenyl optionally substituted by nitro, methyl or methoxy), or representing a protective group for hydroxyl, mercapto or amino, and R$^{20}$ having the same meaning as R$^{18}$ and R$^{19}$ but not representing hydrogen or a protective group, and R$^4$ represents hydrogen or represents methyl, ethyl, tert.-butyl, decyl, 2-chloroethyl, 2,2,2-trichloroethyl, cyanoethyl, diphenylmethyl or triphenylmethyl, acetoxymethyl, allyl, benzyl, 4-methoxybenzyl, 2,4-dimethoxybenzyl, tert.-butyldimethylsilyl, 1-phenoxyethyl or 2-methyl-2-propenyl, 4-nitrobenzyl, 2-nitrobenzyl, trimethylsilylethyl or dimethyl-tert.-butylsilylethyl or represents a radical of the formula

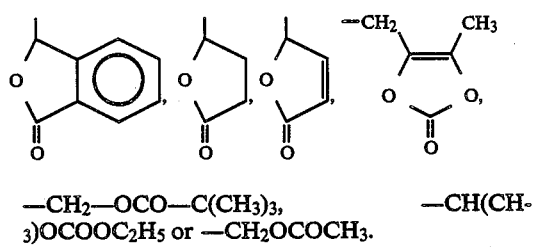

—CH$_2$—OCO—C(CH$_3$)$_3$, —CH(CH$_3$)OCOOC$_2$H$_5$ or —CH$_2$OCOCH$_3$.

Preferred new compounds of the formula I are those in which

R$^1$ represents hydrogen or an amino protective group,

R$^2$ represents hydrogen, chlorine, bromine, azido, represents NHR$^1$, R$^1$ having the abovementioned meaning, represents a radical of the formula

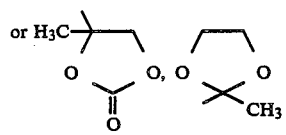

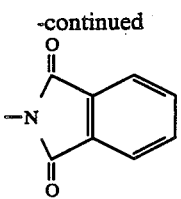

or represents methyl, ethyl, i-propyl, tert.-butyl, or represents

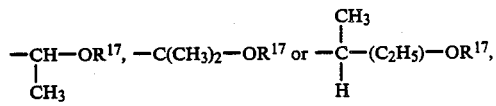

R$^{17}$ representing hydrogen, representing 3,4-dimethoxyphenyl, representing trimethylsilyl, tert.-butyldimethylsilyl, representing benzyloxycarbonyl, 4-nitrobenzyloxycarbonyl, tert.-butoxycarbonyl, allyloxycarbonyl or representing formyl or acetyl, R$^3$ represents phenyl, 3,4-dimethoxyphenyl, represents chlorine, bromine, cyano, cyanato, azido or CF$_3$, or represents —COR$^{18}$, —CONR$^{19}$R$^{18}$, represents allyloxycarbonyl or 4-nitrobenzyloxycarbonyl, represents —NHR$^{18}$, ureido, guanidino, amidino, —NHSO$_2$R$^{20}$, represents —OSO$_2$R$^{20}$, —OPO(OR$^{19}$)OR$^{18}$, represents —S—R$^{18}$, —S-COR$^{18}$, —SO$_2$OR$^{18}$, —SO$_2$NHR$^{18}$, —SCN, —SO$_2$R$^{20}$, —SCONH$_2$ or represents -S-pyridyl, -S-pyrimidyl, -S-methyltetrazolyl, -S-thiadiazolyl, 2-aminothiadiazolyl or represents

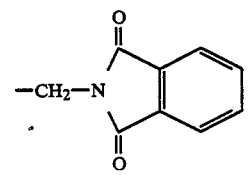

R$^{18}$ and R$^{19}$ being identical or different and representing hydrogen or representing straight-chain or branched alkyl (up to C$_4$), representing phenyl, 4-methylphenyl or benzyl, or representing a protective group for hydroxyl, mercapto or amino, and R$^{20}$ having the same meaning as R$^{19}$ and R$^{18}$ but not representing hydrogen or a protective group, and R$^4$ represents hydrogen or represents methyl, ethyl, tert.-butyl, 2,2,2-trichloroethyl, allyl, acetonyl, 4-nitrobenzyl, 2-nitrobenzyl, 4-methoxybenzyl, benzyl or trimethylsilylethyl, or represents a radical of the formula

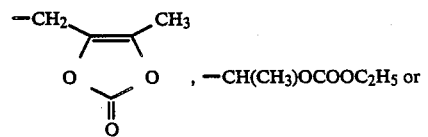

—CH$_2$OCOC(CH$_3$)$_3$.

The terms amino protective group or protective group for hydroxyl or mercapto have the meaning which has already been given above.

Apart from the products detailed in the examples, the following compounds of the general formula (I) are particularly preferred:

| $R^1$ | $R^2$ | $R^3$ | $R^4$ |
|---|---|---|---|
| H | $-\text{CH(CH}_3\text{)OSi(CH}_3\text{)}_3$ | $PhSO_2-$ | $-CH_2-CH=CH_2$ |
| H | " | $CH_3SO_2O-$ | " |
| H | " | $CH_3SO_2-$ | " |
| H | " | $CH_3S-$ | " |
| H | " | $H_2NSO_2-$ | " |
| H | " | $H_2NCOS-$ | " |
| H | " | $(CH_3)_2N-$ | " |
| H | " | $H_2N-$ | " |
| H | " | $PhCH_2NH-$ | " |
| H | " | $CH_3CONH-$ | " |
| H | " | $CHNOH-$ | " |
| H | " | $CH_3SO_2NH-$ | " |
| H | " | $NH_2-\underset{\underset{NH}{\parallel}}{C}-NH-$ | " |
| H | " | $NH_2-\underset{\underset{O}{\parallel}}{C}-NH-$ | " |
| H | " | CHO | " |
| H | $-\text{CH(CH}_3\text{)OSi(CH}_3\text{)}_3$ | $CF_3$ | $-CH_2-CH=CH_2$ |
| H | " | $(CH_3O)_2\underset{\underset{O}{\parallel}}{P}-$ | " |
| H | $-\text{CH(CH}_3\text{)OH}$ | $COO-CH_2-CH=CH_2$ | " |
| H | " | Ph− | " |
| H | " | Cl− | " |
| H | " | $N_3-$ | " |
| H | " | $CH_3SO_2-$ | " |
| H | " | $CF_3$ | " |
| H | $-\text{CH(CH}_3\text{)OSi(CH}_3\text{)}_3$ | $PhSO_2-$ | $-CH_2-\text{C}_6\text{H}_4-NO_2$ |
| H | " | $CH_3SO_2-$ | " |
| H | " | $CH_3S-$ | " |
| H | " | $H_2NSO_2-$ | " |
| H | " | $H_2NCOS-$ | " |
| H | " | $(CH_3)_2N-$ | " |
| H | $-\text{CH(CH}_3\text{)OSi(CH}_3\text{)}_3$ | $H_2N-$ | $-CH_2-\text{C}_6\text{H}_4-NO_2$ |
| H | " | $PhCH_2NH-$ | " |
| H | " | $CH_3CONH-$ | " |
| H | " | $CHONH-$ | " |
| H | " | $CH_3SO_2NH-$ | " |
| H | " | $H_2N-\underset{\underset{NH}{\parallel}}{C}-NH-$ | " |

-continued

| R¹ | R² | R³ | R⁴ |
|---|---|---|---|
| H | " | H₂N−C(=O)−NH− | " |
| H | " | CHO− | " |
| H | " | CF₃ | " |
| H | " | (CH₃O)₂P(=O)− | " |
| H | " | COO−CH₂−C₆H₄−NO₂ | " |
| H | " | CH₃SO₂O− | " |
| H | " | CH₃−C₆H₄−SO₂O | " |
| 4-CH₃O−C₆H₄− | " | Cl− | −CH₂−CH=CH₂ |
| " | " | N₃− | " |
| 4-CH₃O−C₆H₄− | −OSi(CH₃)₂-iPr (with CH₃ stereo) | CH₃SO₂− | −CH₂−CH=CH₂ |
| " | " | CHONH− | " |
| H | −OSi(CH₃)₂C(CH₃)₃ | Cl− | " |
| H | " | N₃− | " |
| H | " | CH₃SO₂− | " |
| H | " | PhSO₂− | " |
| H | " | CH₃S− | " |
| H | " | H₂NSO₂− | " |
| H | " | H₂NCOS− | " |
| H | " | NCS− | " |
| H | " | (CH₃)₂N− | " |
| H | " | H₂N− | " |
| H | " | PhCH₂NH− | " |
| H | −OSi(CH₃)₂C(CH₃)₃ | CH₃CONH− | −CH₂−CH=CH₂ |
| H | " | CH₃SO₂NH− | " |
| H | " | H₂N−C(=NH)−NH− | " |
| H | " | H₂N−C(=O)−NH− | " |
| H | " | CHONH− | " |
| H | " | CHO− | " |
| H | " | CF₃ | " |

-continued

| R¹ | R² | R³ | R⁴ |
|---|---|---|---|
| H | " | (EtO)$_2$P(=O)— | " |
| H | " | Cl— | —CH$_2$—C$_6$H$_4$—NO$_2$ |
| H | " | N$_3$— | " |
| H | " | CH$_3$SO$_2$— | " |
| H | " | PhSO$_2$— | " |
| H | " | CH$_3$S— | " |
| H | —OSi(CH$_3$)$_2$C(CH$_3$)$_3$ (tert-butyldimethylsilyloxy) | PhS— | —CH$_2$—C$_6$H$_4$—NO$_2$ |
| H | " | H$_2$NSO$_2$— | " |
| H | " | H$_2$NCOS— | " |
| H | " | NCS— | " |
| H | " | (CH$_3$)$_2$N— | " |
| H | " | H$_2$N— | " |
| H | " | PhCH$_2$NH— | " |
| H | " | CH$_3$CONH— | " |
| H | " | CHONH— | " |
| H | " | CH$_3$SO$_2$NH— | " |
| H | " | H$_2$N—C(=O)—NH— | " |
| H | " | H$_2$N—C(=O)—NH— | " |
| H | " | H$_2$N—C(=O)— | " |
| H | " | CHO— | " |
| H | —OSi(CH$_3$)$_2$C(CH$_3$)$_3$ | | —CH$_2$—C$_6$H$_4$—NO$_2$ |
| H | " | CF$_3$ | " |
| H | " | (EtO)$_2$P(=O)— | " |
| H | —C(OH)(CH$_3$)$_2$ | Cl | " |
| H | " | CH$_3$SO$_2$— | " |
| H | " | PhSO$_2$— | " |
| H | " | CH$_3$S— | " |

The compounds of the general formula II are known or can be prepared by methods known from the literature [compare German Offenlegungsschrift No. 19 06 401; A. Oida et al., Chem. Pharm. Bull. 29, 2899 (1981), M. Shiozaki et al., Tetrahedron 39, 2399 (1983); M. Shiozaki et al., Tetrahedron 40, 1795 (1984), W. J. Leanza et al., Tetrahedron 39, 2505 (1983), T. Kametani et al., J. Chem. Soc. Perkin I 1981, 2228; J. L. Roberts et al., Synthetic Communications 13, 797 (1983)].

The compounds of the general formula III are known or can be prepared by methods known from the literature [compare S. Julia et al., Compt. Rend. Acad. Sci., Paris, Section C 246, 1890 (1967), European Patent Application No. 78 026, European Pat. No. 52 299, R. M. Kellogg et al., J. C. S. Chem. Comm. (1977) 932].

All inert solvents are suitable as diluents. These preferably include ethers, such as dimethoxyethane, diglyme, triglyme, tetrahydrofuran, dioxane, diethyl ether or tert.-butyl methyl ether, halogenated hydrocarbons, such as dichloromethane, trichloromethane, tetrachloromethane, 1,1,2-trichloroethane, dichloroethane or trichloroethylene, chlorobenzene, dichlorobenzene, ethyl acetate, toluene or cyclohexane.

The reaction is generally carried out at temperatures from −30° C. to +50° C., preferably at room temperature. All tertiary amines are suitable as the bases. Those which may be mentioned as preferred are triethylamine, tripropylamine or tributylamine, ethyl diisopropylamine, pyridine, picoline, lutidine, N-methylmorpholine, N-methylpiperidine, 1,5-diazabicyclo[5.4.0]undec-5-ene (DBU) or 1,5-diazabicyclo[4.3.0]non-3-ene (DBN).

All silylating agents which can also act as Lewis acids are suitable as silylating agents and catalysts. These include, preferably, trialkylsilyl perfluoroalkanesulphonates, trialkylsilyl alkanesulphonates, trialkylsilyl arylsulphonates, trialkylsilyl perfluoroalkanoates, trialkylsilyl alkanoates, trialkylsilyl halides, trialkylsilyl perchlorates, trialkylsilyl difluorophosphates, trialkylsilyl dichlorophosphates, trialkylsilyl fluorosulphonates, N,O-bis(trialkylsilyl)acetamides and trialkylsilyl cyanides. Particularly suitable are trimethylsilyl trifluoromethanesulphonate, trimethylsilyl nonafluorobutanesulphonate, trimethylsilyl trifluoroacetate, trimethylsilyl perchlorate, trimethylsilyl bromide, trimethylsilyl difluorophosphate, trimethylsilyl fluorosulphonate and N,O-bis(trimethylsilyl)trifluoroacetamide.

To carry out the process, it is necessary to introduce first
(a) 0.1–1, preferably 0.5–1, equivalent of the compound II per equivalent of the compound III,
(b) 1–2, preferably 1–1.5, equivalents of silylating agent per equivalent of the compound III, and
(c) 1.01–3, preferably 1.05–2, equivalents of base (amine) per equivalent of silylating agent,
and after 0.1–24 h, preferably 0.1–12 h, to add sufficient additional silylating agent that the silylating agent is then present in a slight excess, preferably in a catalytic excess, over the base (amine).

When carrying out the process, in addition to the abovementioned ratios of amounts of silylating agent and base (amine), one additional equivalent of silylating agent and of base (amine) is to be used for each hydroxyl, mercapto and amino group which is free, that is to say which is to be protected, in the compounds II and III (for example when $R^1 = H$).

The reaction rate substantially depends on the amount of catalyst used, that is to say the excess of silylating agent. The reaction takes place within 0.1 to 48 h, preferably from 0.1 to 24 h.

The compounds of the general formula I are valuable intermediates for the synthesis of effective antibiotics [compare, inter alia, D. H. Shih et al., Heterocycles 21, 29 (1984)].

The examples which follow serve to describe the invention further but without restricting it.

(A) Examples for the preparation of compounds of the formula III:

PREPARATION EXAMPLE 1

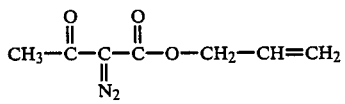

Allyl 2-diazo-3-oxobutanoate 55.4 ml (0.4 mole - 2 equivalents) of triethylamine were added dropwise to a solution, which had been cooled to 0° C., of 28.43 g (0.2 mole) of allyl acetoacetate and 43.39 g (0.22 mole - 1.1 equivalents) of p-toluenesulphonyl azide in 400 ml of anhydrous acetonitrile. The mixture was stirred at 0° C. for 3.5 h, then 50 g of kieselguhr were added, evaporation in vacuo was carried out and then chromatography on 400 g of silica gel (toluene:ethyl acetate 96:4). 31.9 g (95%) of the title compound were obtained as a pale yellow oil, Rf: 0.36 (toluene:ethyl acetate 9:1).

IR (CHCl$_3$) 2141 (N$_2$), 1714 (C=O), 1651 cm$^{-1}$ (C=O).

$^1$H-NMR (200 MHz, CDCl$_3$) δ 2.50 (s, 3H, CH$_3$), 4.76 (m, 2H, —CH$_2$—CH=CH$_2$), 5.3–5.4 (m, 2H, —CH$_2$—CH=CH$_2$), 5.9–6.1 (m, 1H, —CH$_2$—CH=CH$_2$).

C$_7$H$_8$N$_2$O$_3$: (168.2) calculated: C 50.00, H 4.80, N 16.66. found: C 49.9, H 4.8, N 16.6.

PREPARATION EXAMPLE 2

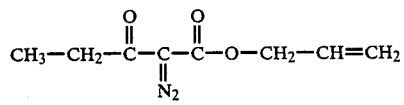

Allyl 2-diazo-3-oxopentanoate a. In analogy to the method described by L. Weiler et al., J. Am. Chem. Soc. 96, 1082 (1974), 8.3 g (27%) of allyl 3-oxopentanoate were obtained as a colorless liquid, boiling point 84° C./14 mm Hg, Rf: 0.34 (toluene:ethyl acetate 9:1), from 28.43 g (0.2 mole) of allyl 3-oxobutanoate and 15 ml (0.24 mole - 1.2 equivalents) of methyl iodide and chromatography of the crude product on 700 g of silica gel (toluene:ethyl acetate 95:5) followed by distillation.

IR (CHCl$_3$) 1741 (C=O), 1714 cm$^{-1}$ (C=O).

$^1$H-NMR (300 MHz, CDCl$_3$) δ 1.10 (t, J=8 Hz, 3H, CH$_2$CH$_3$), 2.60 (q, J=8 Hz, 2H, CH$_2$CH$_3$), 3.48 (s, 2H, CH$_2$), 4.65 (m, 2H, CH$_2$—CH=CH$_2$), 5.2–5.4 (m, 2H, CH=CH$_2$), 5.8–6.0 (m, 1H, CH$_2$—CH=CH$_2$).

C$_8$H$_{12}$O$_3$: (156.2) calculated: C 61.52, H 7.74. found: C 61.4, H 7.8.

b. As described for preparation Example 1, 9.34 g (97%) of the title compound were obtained as a pale yellow oil, Rf: 0.5 (toluene:ethyl acetate 9:1), from 8.3 g (53.1 mmol) of allyl 3-oxopentanoate and chromatography of the crude product on 130 g of silica gel (toluene:ethyl acetate 96:4).

IR (CHCl$_3$) 2137 (N$_2$), 1712 (C=O), 1650 cm$^{-1}$ (C=O).

$^1$H-NMR (200 MHz, CDCl$_3$) δ 1.16 (t, J=8 Hz, 3H, CH$_3$), 2.89 (q, J=8 Hz, 2H, CH$_2$CH$_3$), 5.52 (m, 2H, CH$_2$—CH=CH), 5.3–5.4 (m, 2H, CH=CH$_2$), 5.9–6.1 (m, 1H, CH$_2$—CH=CH$_2$).

C$_8$H$_{10}$N$_2$O$_3$: (182.2) calculated: C 52.74, H 5.53, N 15.38. found: C 52.1, H 5.5, N 14.8.

PREPARATION EXAMPLE 3

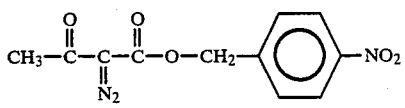

4-Nitrobenzyl 2-diazo-3-oxobutanoate 35.0 ml (0.25 mole - 1.8 equivalent) of triethylamine were added dropwise to a solution, which had been cooled to 0° C., of 33.18 g (0.14 mole) of 4-nitrobenzyl acetoacetate and 30.40 g (0.15 mole) of p-toluenesulphonyl azide in 280 ml of anhydrous acetonitrile. The mixture was stirred at 0° C. for 2 h, and then the resulting precipitate was filtered off with suction, washed with ether and dried over $P_4O_{10}$ under high vacuum. 20.3 g (55%) of the title compound were obtained as colorless crystals, melting point 132° C. A further 6.3 g (17%) of the title compound were obtained by chromatography of the filtrate solution on 400 g of silica gel (toluene-:ethyl acetate 9:1), Rf: 0.35 (toluene:ethyl acetate 9:1).

IR (KBr) 2144 ($N_2$), 1709 (C=O), 1662 (C=O), 1514 ($NO_2$ asym.), 1343 cm$^{-1}$ ($NO_2$ sym.).

$^1$H-NMR (200 MHz, DMSO) δ 2.44 (s, 3H, $CH_3$), 5.44 (s, 2H, $CH_2$), 7.72 (d, J=9 Hz, 2H, $H_{arom.}$), 8.28 (d, J=9 Hz, 2H, $H_{arom.}$).

$C_{11}H_9N_3O_5$: (263.2) calculated: C 50.20, H 3.45, N 15.96. found: C 50.2, H 3.4, N 15.9.

PREPARATION EXAMPLE 4

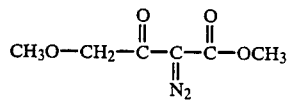

Methyl 2-diazo-4-methoxy-3-oxobutanoate

As described for preparation Example 1, 3.05 g (89%) of the title compound were obtained as a pale yellow oil, Rf: 0.35 (toluene:ethyl acetate 3:1), from 2.92 g (20 mmol) of methyl 4-methoxyacetoacetate and chromatography of the crude product on 900 g of silica gel (toluene:ethyl acetate 3:1).

IR (CHCl$_3$) 2138 ($N_2$), 1711 (C=O), 1665 cm$^{-1}$ (C=O).

$^1$H-NMR (250 MHz, CDCl$_3$) δ 3.48 (s, 3H, COOCH$_3$), 3.86 (s, 3H, OCH$_3$), 4.53 (s, 2H, CH$_2$).

$C_6H_8N_2O_4$: (172.1) calculated: C 41.86, H 4.68, N 16.27. found: C 42.1, H 4.7, N 16.6.

PREPARATION EXAMPLE 5

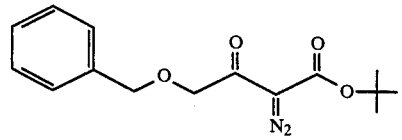

tert.-Butyl 4-benzyloxy-2-diazo-3-oxobutanoate 5.54 ml (40 mmol - 2 equivalents) of triethylamine were added dropwise to a solution, which had been cooled to 0° C., of 5.29 g (20 mmol) of tert.-butyl 4-benzyloxyacetoacetate and 4.34 g (22 mmol) of p-toluenesulphonyl azide in 40 ml of anhydrous acetonitrile. The mixture was stirred at 0° C. for 30 min, 8 g of kieselguhr were added, and evaporation in vacuo and chromatography on 100 g of silica gel (toluene:ethyl acetate 95:5) were carried out. 3.98 g (69%) of the title compound were obtained as colorless crystals, melting point: 68° C., Rf: 0.31 (toluene:ethyl acetate 95:5).

IR (KBr) 2144 ($N_2$), 1700, 1673 cm$^{-1}$.

$^1$H-NMR (300 MHz, CDCl$_3$) δ 1.51 (s, 9H, C(CH$_3$)$_3$), 4.59 (s, 2H, CH$_2$), 4.67 (s, 2H, CH$_2$), 7.3-7.5 (m, 5H, Ph).

$C_{15}H_{18}N_2O_4$: (290.3) calculated: C 62.06, H 6.23, N 9.65. found: C 62.1, H 6.2, N 9.6.

PREPARATION EXAMPLE 6

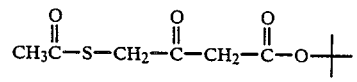

tert.-Butyl 4-acetylthioacetoacetate 2.40 g (21.0 mmol) of dry potassium thioacetate were added to a solution, which had been cooled to 0° C., of 3.85 g (20.0 mmol) of tert.-butyl 4-chloroacetoacetate in 40 ml of anhydrous acetonitrile, and the mixture was stirred at this temperature for 30 min. It was then poured into a mixture of NaCl solution and ethyl acetate, the organic phase was separated off, extraction with 2×30 ml of ethyl acetate was carried out, and the extract was washed with water and dried over MgSO$_4$. After evaporation of the solvent in vacuo and chromatography of the residue on 60 g of silica gel (toluene-:ethyl acetate 95:5), 3.87 g (83%) of the title compound were obtained as a colorless oil, Rf: 0.24 (toluene:ethyl acetate 95:5).

IR (CHCl$_3$) 1740-1710 cm$^{-1}$ (C=O).

$^1$H-NMR (250 MHz, CDCl$_3$) δ 1.50 (s, 9H, C(CH$_3$)$_3$), 2.42 (s, 3H, CH$_3$CO), 3.53 (s, 2H, CH$_2$), 3.90 (s, 2H, CH$_2$).

PREPARATION EXAMPLE 7

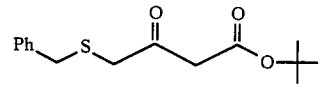

tert.-Butyl 4-benzylthioacetoacetate 7.04 ml (60 mmol) of benzylmercaptan were slowly added dropwise to a suspension of 1.8 g (60 mmol) of sodium hydride (80% in liquid paraffin) in 50 ml of anhydrous THF at room temperature. The mixture was then stirred for 15 min and subsequently cooled to 0° C. At this temperature, a solution of 10.57 g (55 mmol) of tert.-butyl 4-chloroacetoacetate in 23 ml of THF was added within 1 h. The icebath was removed, and the mixture was stirred for a further 1 h at room temperature and then neutralized by addition of a few drops of 10% strength HCl. The solvent was evaporated in vacuo, ether was added several times, and the extracts were washed with water and dried over MgSO$_4$. Evaporation of the ether in vacuo produced an oil which was purified by chromatography on 800 g of silica gel (toluene). 12.74 g (83%) of the title compound were obtained in the form of a colorless oil, Rf: 0.13 (toluene).

IR (CHCl$_3$) 1740-1710 cm$^{-1}$ (C=O, β-keto ester).

$^1$H-NMR (200 MHz, CDCl$_3$) δ 1.49 (s, 9H, C(CH$_3$)$_3$), 3.22 (s, 2H, CH$_2$), 3.52 (s, 2H, CH$_2$), 3.68 (s, 2H, CH$_2$), 7.33 (s, 5H, Ph).

$C_{15}H_{20}O_3S$: (280.4) calculated: C 64.3, H 7.2, S 11.4. found: C 64.3, H 7.2, S 11.3.

PREPARATION EXAMPLE 8

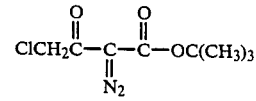

tert.-Butyl 4-chloro-2-diazo-3-oxobutanoate

As described for Preparation Example 1, 2.67 g (84%) of the title compound were obtained as crystals, Rf: 0.29 (toluene), melting point: 40°–41° C., from 2.79 g (14.5 mmol) of tert.-butyl 4-chloroacetoacetate and filtration of the crude product on 30 g of silica gel (toluene).

IR (CHCl$_3$): 2140 (N$_2$), 1708 (C=O), 1662 cm$^{-1}$.

$^1$H-NMR (300 MHz, CDCl$_3$) δ 1.54 (s, 9H, C(CH$_3$)$_3$), 4.60 (s, 2H, CH$_2$).

C$_8$H$_{11}$N$_2$O$_3$Cl: (218.6) calculated: C 43.9, H 5.1, N 12.8. found: C 44.0, H 5.1, N 13.3.

PREPARATION EXAMPLE 9

$$CH_3COSCH_2\overset{O}{\overset{\|}{C}}-\underset{\underset{N_2}{\|}}{C}-\overset{O}{\overset{\|}{C}}-OC(CH_3)_3$$

tert.-Butyl 4-acetylthio-2-diazo-3-oxobutanoate

As described for Preparation Example 1, 3.48 g (45%) of the title compound were obtained as an oil, Rf: 0.34 (toluene:ethyl acetate 95:5), from 6.97 g (30.0 mmol) of tert.-butyl 4-acetylthioacetoacetate after chromatography of the crude product on 280 g of silica gel.

IR (CHCl$_3$) 2140 (N$_2$), 1705 (C=O) 1656 cm$^{-1}$.

$^1$H-NMR (300 MHz, CDCl$_3$), 1.55 (s, 9H, C(CH$_3$)$_3$), 2.39 (s, 3H, COCH$_3$), 4.23 (s, 2H, CH$_2$).

C$_{10}$H$_{14}$N$_2$O$_4$S: (258.3) calculated: C 46.5, H 5.5, N 10.8. found: C 46.5, H 5.4, N 11.3.

PREPARATION EXAMPLE 10

$$PhCH_2-S-CH_2-\overset{O}{\overset{\|}{C}}-\underset{\underset{N_2}{\|}}{C}-\overset{O}{\overset{\|}{C}}-O-C(CH_3)_3$$

tert.-Butyl 4-benzylthio-2-diazo-3-oxobutanoate

As described for Preparation Example 1, 3.4 g (74%) of the title compound were obtained as a yellow oil, Rf: 0.28 (toluene), from 4.21 g (15.0 mmol) of tert.-butyl 4-benzylthioacetoacetate after chromatography of the crude product on 100 g of silica gel (toluene).

IR (CHCl$_3$) 2145 (N$_2$), 1705, 1635 cm$^{-1}$.

$^1$H-NMR (250 MHz, CDCl$_3$) δ 1.52 (s, 9H, C(CH$_3$)$_3$), 3.58 (s, 2H, CH$_2$), 3.77 (s, 2H, CH$_2$), 7.3–7.4 (m, 5H, Ph).

C$_{15}$H$_{18}$N$_2$O$_3$S: (306.38) calculated: C 58.80, H 5.92, S 10.46. found: C 59.2, H 6.0, S 10.5.

PREPARATION EXAMPLE 11

[Phthalimide]N—CH$_2$—CH$_2$—$\overset{O}{\overset{\|}{C}}$—CH$_2$—$\overset{O}{\overset{\|}{C}}$—O—CH$_2$—CH=CH$_2$

Allyl 3-oxo-5-phthalimidopentanoate

A solution of 2.89 g (10.0 mmol) of ethyl 3-oxo-5-phthalimidopentanoate in 14 ml of allyl alcohol was heated at 80° C. in the presence of catalytic amounts of p-toluenesulphonic acid hydrate for 3 days. The solvent was then evaporated in vacuo and the residue was purified by chromatography on 170 g of silica gel (toluene:ethyl acetate 4:1). The title compound was obtained as colorless crystals, melting point: 53°–55° C., Rf: 0.40 (toluene:ethyl acetate 4:1).

IR (CHCl$_3$) 1716 cm$^{-1}$ (C=O).

$^1$H-NMR (300 MHz, CDCl$_3$) 3.01 (t, J=7 Hz, 2H, CH$_2$CO), 3.54 (s, 2H, COCH$_2$CO), 4.0 (t, J=7 Hz, 2H, CH$_2$N), 4.65 (m, 2H, C$\underline{H}_2$—CH=CH$_2$), 5.2–5.4 (m, 2H, CH=C$\underline{H}_2$), 5.8–6.0 (m, 1H, CH$_2$—C$\underline{H}$=CH$_2$), 7.73, 7.87 (m, each 2H, H$_{arom.}$).

C$_{16}$H$_{15}$NO$_5$: (301.3) calculated: C 63.78, H 5.02, N 4.64. found: C 63.8, H 5.4, N 4.3.

PREPARATION EXAMPLE 12

$$(C_2H_5O)_2\overset{O}{\overset{\|}{P}}-CH_2-\overset{O}{\overset{\|}{C}}-CH_2-\overset{O}{\overset{\|}{C}}-O-CH_2-CH=CH_2$$

Allyl 4-(diethylphosphinyl)-3-oxobutanoate

A solution of allyl 4-bromo-3-oxobutanoate (German Offenlegungsschrift No. 2,048,470) in 10 ml of THF was slowly added dropwise to a suspension, which had been cooled to −30° C., of 300 mg (10.0 mmol) of sodium hydride in THF. The mixture was stirred at −30° C. for 15 min and then 0.65 ml (5.02 mmol) of diethyl phosphite was added dropwise. The cooling bath was removed and the mixture was stirred at room temperature for 30 min. To work up, the mixture was poured into a mixture of ethyl acetate and saturated NaHCO$_3$ solution, extraction with ethyl acetate was carried out, followed by washing with saturated NaCl solution and drying over MgSO$_4$.

After evaporation of the solvent in vacuo and chromatography of the residue on 90 g of silica gel (toluene:ethyl acetate 1:4), 705 mg (51%) of the title compound were obtained as an oil, Rf: 0.30 (toluene:ethyl acetate 1:4).

IR (CHCl$_3$) 1735, 1718, 1640, 1250 cm$^{-1}$ (P=O).

$^1$H-NMR (300 MHz, CDCl$_3$) δ 1.35 (t, J=7.5 Hz, 6H, CH$_3$CH$_2$), 3.26 (d, J=23 Hz, 2H, PCH$_2$CO), 3.71 (s, 2H, $\overline{COCH_2CO}$), 4.17 (q, J=7.5 Hz, 4H, CH$_3$C$\underline{H}_2$), 4.66 (m, CH$_2$—CH=CH$_2$), 5.2–5.4 (m, 2H, C$\underline{H}$=CH$_2$), 5.8–6.0 (m, 1H, CH$_2$—C$\underline{H}$=CH$_2$).

PREPARATION EXAMPLE 13

$$Ph-\overset{O}{\underset{\underset{O}{\|}}{\overset{\|}{S}}}-CH_2-\overset{O}{\overset{\|}{C}}-\underset{\underset{N_2}{\|}}{C}-\overset{O}{\overset{\|}{C}}-O-CH_2-CH=CH_2$$

Allyl 2-diazo-3-oxo-4-phenylsulphonylbutanoate 2.59 g (15.0 mmol) of m-chloroperbenzoic acid were added to a solution, which had been cooled to 0° C., of 1.38 g (5.0 mmol) of allyl 2-diazo-3-oxo-4-phenylthiobutanoate in 10 ml of dichloromethane, and the mixture was stirred at this temperature for 1 h. To work up, it was poured into saturated NaHCO₃ solution, and extraction with ethyl acetate was carried out, followed by washing with water and drying over MgSO₄. After evaporation of the solvent in vacuo and filtration of the crude product on 30 g of silica gel (toluene:ethyl acetate 9:1), 883 mg (57%) of the title compound were obtained, Rf: 0.24 (toluene:ethyl acetate 95:5).

IR (CHCl₃) 2150 (N₂), 1716, 1647, 1328 (SO₂ as.), 1160 cm$^{-1}$ (SO₂ sym.).

$^1$H-NMR (200 MHz, CDCl₃) δ 4.78 (d, J=7 Hz, 2H, C$\underline{H_2}$—CH=CH₂), 4.88 (s, 2H, SO₂CH₂CO), 5.4–5.5 (m, 2$\underline{H}$, CH=C$\underline{H_2}$), 5.9–6.1 (m, 1H, CH₂—C$\underline{H}$=CH₂), 7.55–7.75 (m, 3H, Ph), 8.02 (m, 2H, Ph).

C₁₃H₁₂N₂O₅S (308.3): calculated: C 50.64, H 3.92, N 9.09, S 10.40. found: C 50.3, H 3.9, N 8.9, S 10.4.

PREPARATION EXAMPLE 14

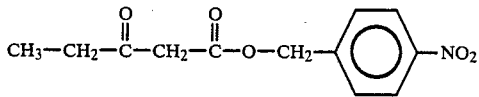

4-Nitrobenzyl 3-oxopentanoate

A suspension of 55.3 g (0.36 mole) of 4-nitrobenzyl alcohol and 56.2 g (0.39 mole) of ethyl 3-oxopentanoate in 360 ml of toluene was heated to boiling. About 300 ml of toluene were distilled out over the course of 10 h, then the mixture was cooled and another 200 ml were added and this procedure was repeated. After cooling, the mixture was filtered through kieselguhr, which was washed with toluene, and the filtrate solution was evaporated in vacuo. 89 g (98%) of the title compound were obtained as an oil, Rf: 0.42 (toluene:ethyl acetate 4:1).

IR (CHCl₃), 1751 (C=O), 1722 (C=O), 1524 (NO₂ asym.), 1351 cm$^{-1}$ (NO₂ sym.).

$^1$H-NMR (300 MHz, CDCl₃) δ 1.10 (t, J=7.5 Hz, 3H, C$\underline{H_3}$CH₂), 2.59 (q, J=7.5 Hz, 2H, CH₃C$\underline{H_2}$), 3.57 (s, 2H, COCH₂CO), 5.29 (s, 2H, CO₂CH₂), 7.53 (d, J=9 Hz, 2H, H$_{arom.}$), 8.20 (d, J=9 Hz, 2H, H$_{arom.}$).

In analogy to the preparation examples already described, the following 4-substituted acetoacetic esters were also obtained (Preparation Examples 15–21, Table 1):

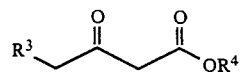

From these were obtained, as described for Preparation Example 1, the corresponding diazo compounds by diazo transfer (Preparation Examples 22–34, Table 2):

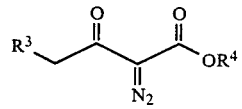

TABLE 1

| Prep. Ex. No. | R³ | R⁴ | prepared by Prep. Ex. | Yield % | Rf (Tol.: Ethylac.) | IR (cm⁻¹) | 1-HNMR (200 MHz, CDCl₃) δ ppm | | Analysis |
|---|---|---|---|---|---|---|---|---|---|
| 15 | CH₂COS— | —CH₂—CH=CH₂ | 6 | 73 | 0.24 (95:5) | 1724 1697 | 2.36 (s, 3H, CH₂CO), 3.60 (s, 2H, COCH₂CO), 3.84 (s, 2H, $\underline{CH_2}$SOCH₂), 4.62 (m, 2H, $\underline{CH_2}$—CH=CH₂), 5.2–5.4 (m, 2H, CH=$\underline{CH_2}$), 5.8–6.0 (m, 1H, CH₂—$\underline{CH}$=CH₂). | calc: fd: | C₉H₁₂O₄S (216.3) C 49.99 H 5.59 S 14.82 C 50.0 N 5.6 S 14.7 |
| 16 | (phenyl) | —CH₂—CH=CH₂ | 11 | 40 | 0.36 (95:5) | 1744 1721 | 3.50 (s, 2H, COCH₂CO), 3.85 (s, 2H, CH₂Ph), 4.63 (m, 2H, $\underline{CH_2}$—CH=CH₂), 5.2–5.4 (m, 2H, CH=$\underline{CH_2}$), 5.8–6.0 (m, 1H, CH₂—$\underline{CH}$=CH₂). | calc: fd: | C₁₃H₁₄O₃ (218.2) C 71.54 N 6.47 C 71.5 N 6.7 |
| 17 | (N-methylthiotriazole) | —CH₂—CH=CH₂ | 6 | 86 | 0.27 (7:3) | 1738 (sh) 1719 1650 | 3.74 (s, 2H, COCH₂CO), 3.97 (s, 3H, NCH₂), 4.41 (s, 2H, SCH₂CO), 4.76 (m, 2H, $\underline{CH_2}$—CH=CH₂), 5.25–5.4 (m, 2H, CH=$\underline{CH_2}$), 5.8–6.0 (m, 1H, CH₂—$\underline{CH}$=CH₂). | calc: fd: | C₉H₁₂N₄O₃S (256.3) C 42.18 N 4.72 N 21.86 S 12.51 C 42.0 H 4.7 N 21.5 N 12.5 |
| 18 | N₃ | —CH₂—CH=CH₂ | 12, but only 1 equivalent of NaH | 43 | 0.34 (95:5) | 2110 (N₃) 1740 (sh) 1725 | 3.58 (s, 2H, COCH₂CO), 4.15 (s, 2H, N₃CH₂CO), 4.69 (m, 2H, $\underline{CH_2}$—CH=CH₂), 5.3–5.5 (m, 2H, CH=$\underline{CH_2}$), 5.9–6.1 (m, 1H, CH₂—$\underline{CH}$=CH₂). | calc: fd: | C₇H₉N₃O₃ (183.2) C 45.90 N 4.95 C 45.8 N 4.9 |
| 19 | COO—CH₂—CH=CH₂ | —CH₂—CH=CH₂ | 11 | 28 | 0.29 (96:4) | 1735 1720 1655 | 3.66 (s, 4H, COCH₂CO), 4.64 (m, 4H, $\underline{CH_2}$—CH=CH₂), 5.25–5.3 (m, 4H, CH=$\underline{CH_2}$), 5.85–6.0 (m, 2H, CH₂—$\underline{CH}$=CH₂). | calc: fd: | C₁₁H₁₄O₄ (226.2) C 58.40 N 6.24 C 58.4 N 6.3 |
|  | COOCH₂ | —CH₂—CH=CH₂ | from dimethyl ester | +16 | 0.21 (96:4) | 1740 1720 1650 | 3.64 (s, 2H, CH₂), 3.66 (s, 2H, CH₂), 3.77 (s, 3H, COOCH₂), 4.66 (m, 2H, $\underline{CH_2}$—CH=CH₂), 5.25–5.4 (m, 2H, CH=$\underline{CH_2}$), 5.8–6.0 (m, 1H, CH₂—$\underline{CH}$=CH₂). | calc: fd: | C₉H₁₁O₃ C 54.27 N 5.57 C 54.0 N 6.0 |

TABLE 1-continued

| Prep. Ex. No. | R³ | R⁴ | prepared by Prep. Ex. | Yield % | Rf (Tol.: Ethylac.) | IR (cm⁻¹) | 1-HNMR (200 MHz, CDCl₃) δ ppm | Analysis |
|---|---|---|---|---|---|---|---|---|
| 20 | phenyl | −CH₂−C₆H₄−NO₂ (para) | 14 | 98 | 0.31 (95:5) | — | 3.54 (s, 2H, COCH₂CO), 3.86 (s, 2H, CH₂Ph), 5.27 (s, 2H, COOCH₂), 7.51 (d, J=9 Hz, 2H, Harom.), 8.20 (d, J=9 Hz, 2H, Harom.). | — |
| 21 | 3,4-(CH₃O)(CH₂O)−C₆H₃−CH₂− | −CH₂−C₆H₄−NO₂ (para) | 14 | 97 | 0.40 (7:3) | — | 3.55 (s, 2H, CH₂), 3.76 (s, 2H, CH₂), 3.85 (s, 3H, OCH₃), 3.86 (s, 3H, OCH₃), 5.23 (s, 2H, CO₂CH₂), 6.7–6.9 (m, 3H, Harom.), 7.50 (d, J=9 Hz, 2H, Harom.), 8.22 (d, J=9 Hz, 2H, Harom.). | — |
| 21 (a) | CF₃ | −CH₂−CH=CH₂ | acc. to K. P. Zeiler Synthesis (1985) 334. | 22 | 0.42 (9:1) | 1718 1650 | 3.46 (q, J=11 Hz, 2H, CF₃C$\underline{H}$₂), 3.60 (s, 2H, COCH₂CO), 4.67 (m, 2H, −CH₂−CH=CH₂), 5.2–5.4 (m, 2H, −CH=C$\underline{H}$₂), 5.85–6.0 (m, 1H, −C$\underline{H}$=CH₂). | bp.: 140–150° C./ 10 mm (Kugelrohr) |

TABLE 2

| Prep. Ex. No. | R³ | R⁴ | Yield % | Rf (Tol.:Ethylac.) | IR (cm⁻¹) | ¹H—NMR (200 MHz, CDCl₃) δppm | Analysis |
|---|---|---|---|---|---|---|---|
| 22 | Cl | —CH₃—CH—CH₃ | 76 | 0.24 (1:0) | 2147 (N₃) 1714 1666 | 4.64 (s, 2H, CH₂Cl), 4.76 (m, 2H, CH₃—CH—CH), 5.3–5.4 (m, 2H, CH—CH₃), 5.85–6.05 (m, 1H, CH₃—CH—CH₃). | C₂H₃ClN₃O₃ (202.6) calc: C 41.50 N 3.48 N 13.8 fd: C 41.7 H 3.6 N 13.8 |
| 23 | CH₃COS | —CH₃—CH—CH₃ | 89 | 0.31 (95:5) | 2144 (N₃) 1715 1658 1327 | 2.39 (s, 3H, CH₃CO), 4.25 (s, 2H, CH₃SCOCH₃), 4.77 (m, 2H, CH₃—CH—CH), 5.3–5.4 (m, 2H, CH—CH₃), 5.9–6.0 (m, 1H, CH₃—CH—CH₃). | C₉H₁₀N₃O₄S (242.3) calc: C 44.62 N 4.16 N 11.56 S 13.23 fd: C 45.0 N 4.2 N 11.5 N 13.6 |
| 24 | —C₆H₅ (Ph) | —CH₃—CH—CH₃ | 88 | 0.21 (1:0) | 2143 (N₃) 1715 1649 | 4.21 (2, 2H, PhCH₂), 4.77 (m, 2H, CH₃—CH—CH₃), 5.3–5.4 (m, 2H, CH—CH₃), 5.9–6.1 (m, 1H, CH₃—CH—CH₃), 7.32 (m, 5H, Ph). | C₁₃H₁₂N₃O₃ (244.3) calc: C 63.93 N 4.95 N 11.47 fd: C 63.8 N 5.0 N 11.7 |
| 25 | N-methylphthalimide | —CH₃—CH—CH₃ | 80 | 0.34 (9:1) | 2143 (N₃) 1718 1650 | 3.25 (t, J=7 Hz, 2H, CH₃CO), 4.05 (t, J=7 Hz, 2H, CH₃N), 4.70 (m, 2H, CH₃—CH—CH₃), 5.3–5.4 (m, 2H, CH—CH₃), 5.8–6.0 (m, 1H, CH₃—CH—CH₃), 7.70, 7.85 (m, je 2H, Harom). | C₁₆N₁₃N₃O₃ (327.3) calc: C 58.72 N 4.00 N 12.84 fd: C 58.7 N 4.0 N 12.8 |
| 26 | 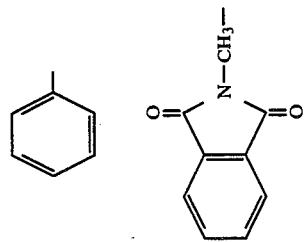 | —CH₂—CH—CH₃ | 97 | 0.23 (4:1) | 2134 (N₃) 1712 1655 | 4.01 (s, 3H, NCH₃), 4.72 (s, 2H, SCH₃CO), 4.79 (m, 2H, CH₃—CH—CH₃), 5.35–5.45 (m, 2H, CH—CH₃), 5.9–6.1 (m, 1H, CH₃—CH—CH₃). | C₉H₁₀N₆O₃S (282.3) calc: C 38.30 N 3.57 N 29.77 S 11.36 fd: C 38.6 N 3.7 N 29.5 S 11.2 |
| 27 | N₃ | —CH₃—CH—CH₃ | 34 68.4⁽ᵃ⁾ | 0.39 (95:5) | 2135 (N₃) 2110 1710 1660 | 4.40 (s, 2H, H₃CH₃CO), 4.74 (m, 2H, CH₃—CH—CH₃), 5.3–5.4 (m, 2H, CH—CH₃), 5.85–6.0 (m, 1H, CH₃—CH—CH₃). | |
| 28 | NCS— | —CH₃—CH—CH₃ | 76⁽ᵇ⁾ | 0.29 (95:5) | 2146 (N₃ SCN) 1713 1655 | 4.33 (s, 2H, NCSCH₃CO), 4.77 (m, 2H, CH₃—CH—CH₃), 5.3–5.4 (m, 2H, CH—CH₃), 5.9–6.05 (m, 1H, CH₃—CH—CH₃). | C₆N₃H₃O₃S (225.2) calc: C 42.66 N 3.13 N 18.66 S 14.23 fd: C 42.9 N 3.1 N 18.7 S 14.1 |

TABLE 2-continued

| Prep. Ex. No. | R³ | R⁴ | Yield % | Rf (Tol.:Ethylac.) | IR (cm⁻¹) | ¹H—NMR (200 MHz,CDCl₃)δppm | Analysis |
|---|---|---|---|---|---|---|---|
| 29 | CH₃—CH—CH₃—OOC— | —CH₃—CH—CH₃ | 30 | 0.31 (95:5) | 2147 (N₃) 1718 1655 | 3.90 (s, 2H, COCH₃CO), 4.64 (m, 2H, CH₃—CH—CH₃), 4.72 (m, 2H, CH₃—CH—CH₃), 5.2–5.4 (m, 4H, CH—CH₃), 5.85–6.0 (m, 2H, CH—CH₃). | C₁₁N₁₃H₃O₃ (252.2) calc: C 52.38 N 4.80 N 11.11 fd: C 52.4 H 4.9 N 11.0 |
| 30 | (C₃H₅O₃)P(=O)— | —CH₃—CH—CH₃ | 67 | 0.35 (0:1) | 2150 (N₃) 1715 1645 1255 (P=O) | 1.34 (t, J=6 Hz, 6N, CH₃CH₃), 3.70 (d, J=23 Hz, 2H, PCH₃CO), 4.16 (q, J=6 Hz, 4H, CH₃ CH₃), 4.75 (m, 2H, —CH₃—CH—CH₃), 5.3–5.45 (m, 2H, —CH—CH₃), 5.9–6.05 (m, 1H, —CH₃—CH—CH₃). | C₁₁H₁₂N₃O₆P calc: C 43.43 H 5.63 N 9.21 P 10.18 fd: C 43.6 N 5.6 N 9.4 P 9.7 |
| 31 | PhS | —CH₃—CH—CH₃ | 90(c) | 0.55 (95:5) | 2150 (N₃) 1715 1650 | 4.18 (s, 2H, SCH₃CO), 4.78 (m, 2H, CH₃—CH—CH₃), 5.3–5.5 (m, 2H, CH—CH₃), 5.9–6.1 (m, 1H, CH₃—CH—CH₃), 7.3–7.6 (m, 5H, Ph). | |
| 32 | CH₃— | —CH₂—C₆H₄—NO₂ | 71 | 0.56 (4:1) | 2145 (N₃) 1713 1659 1519 (NO₂as.) 1352 (NO₂s.) | 1.14 (t, J=7.5 Hz, 3H, CH₂CH₃), 2.86 (q, J=7.5 Hz, 2H, CH₃ CH₃), 5.34 (s, 2H, CO₂CH₃), 7.55 (d, J=9 Hz, 2H, Harom.), 8.25 (d, J=9 Hz, 2H, Harom.). | C₁₂H₁₁N₃O₃ (277.29) Ber.: C 51.99 H 4.00 N 15.16 Gef.: C 52.1 H 4.0 N 15.2 |
| 33 | C₆H₅— | —CH₂—C₆H₄—NO₂ | 61 | 0.40 (95:5) | 2133 (N₃) 1720 1655 1522 (NO₂as.) 1350 (NO₂s.) | 4.19 (s, 2H, PhCH₃), 5.38 (s, 2H. COOCH₂), 7.2–7.5 (m, 5H, Ph), 7.52 (d, J=9 Hz, 2H, Harom.), 8.25 (d, J=9 Hz, 2H, Harom.). | (Schmp.: 74–76° C.) |
| 34 | 3,4-(CH₃O)₂C₆H₃— | —CH₂—C₆H₄—NO₂ | 84 | 0.30 (4:1) | 2155 (N₃) 1715 1658 1516 (NO₃as) 1349 (NO₃s) | 3.81,3.82 (s, 6H, OCH₃), 4.03 (s 2H, ArCH₃CO), 5.33 (s, 2H, COOCH₂), 6.76 (m, 3H, Harom.), 7.48 (d, J=9 Hz, 2H, Harom.), 8.18 (d, J=9 Hz, 2H, Harom.). | C₁₉H₁₇N₃O₇ (399.4) Ber.: C 57.14 H 4.29 N 10.52 Geb.: C 56.7 H 4.4 N 10.1 |
| 34(a) | CF₃ | —CH₃—CH—CH₃ | 77 | 0.57 (9:1) | 2135 (N₃) 1710 1655 | 3.79 (q, J=10 Hz, 2H, CF₃ CH₃), 4.76 (d, J=6 Hz, 2H, —CH₃—CH—CH₃), 5.3–5.45 (m, 2H, —CH—CH₃), 5.85–6.05 (m, 1H, —CH₃—CH—CH₃). | |

(a)Preparation Example 18 + NaN₃ (1.3 equivalent) in DMF 1 h 0° C.
(b)Preparation Example 18 + KSCN (1.2 equivalent) 40 h room temperature
(c)Preparation Example 18 + PhSNa (1.2 equivalent) in THF 3 h 0° C.

(B) Examples of the preparation of compounds of the formula I by the process according to the invention.

EXAMPLE 1

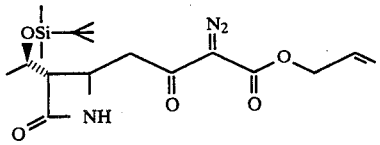

(3S,4R)-3-[(1R)-1-tert.-Butyldimethylsilyloxyethyl]-4-[3-allyloxycarbonyl-3-diazo-2-oxopropyl]azetidin-2-one 7.2 ml (52 mmol - 2.6 equivalents) of triethylamine are added to a solution, which has been cooled to 0° C., of 5.75 g (20 mmol) of (3R,4R)-4-acetoxy-3-[(1R)-1-tert.-butyldimethylsilyloxyethyl]azetidin-2-one [S. Oida et al. Chem. Pharm. Bull. 29 2899 (1981); M. Shiozaki et al. Tetrahedron 39 2399 (1983)] and 4.37 g (26 mmol - 1.3 equivalents) of allyl 2-diazo-3-oxobutanoate in 190 ml of anhydrous dichloromethane, and then 9.3 ml (48 mmol - 2.4 equivalents) of trimethylsilyl trifluoromethanesulphonate are added dropwise. The cooling bath was removed, and the mixture was stirred at room temperature for 1 h, 1.55 ml (8 mmol - 0.4 equivalent) of trimethylsilyl trifluoromethanesulphonate were added, and the mixture was stirred for a further 0.5 h at room temperature. The reaction solution was then poured into a mixture of cold, saturated NaHCO3 solution and ethyl acetate, and extraction with ethyl acetate was carried out, and the combined organic extracts were washed with saturated NaCl solution and dried over MgSO4. The solvent was evaporated in vacuo, and the residue was filtered through 150 g of silica gel (toluene:ethyl acetate 4:1). 6.4 g (81%) of the title compound were obtained as pale crystals, melting point: 66° C., Rf: 0.33 (toluene-:ethyl acetate 7:3) $[\alpha]_D^{20}=59.2°$ (c 0.969, CHCl3).

IR (CHCl3) 2144 (N2), 1761 (C=O, β-lactam), 1714, 1649 cm$^{-1}$.

$^1$H-NMR (250 MHz, CDCl3) δ 0.06 (s, 6H, CH3Si), 0.88 (s, 9H, CH3C—Si), 1.23 (d, J=6 Hz, 3H, CH3CH), 2.90 (dd, J=2 Hz, 5 Hz, 1H, H-3), 3.03 (dd, J=10 Hz, 17.5 Hz, 1H, CH2CO), 4.06 (ddd, J=3 Hz, 5 Hz, 10 Hz, 1H, H-4), 4.24 (dq, J=5 Hz, 6 Hz, 1H, CH3CH), 4.78 (m, 2H, CH2—CH=CH), 5.3–5.5 (m, 2H, CH=CH2), 5.9–6.1 (m, CH2—CH=CH2), 6.07 (bs, NH) together 2H.

C18H29N3O5Si (395.5): calculated: C 54.66, H 7.39, N 10.62. found: C 54.3, H 7.4, N 10.4.

EXAMPLE 2

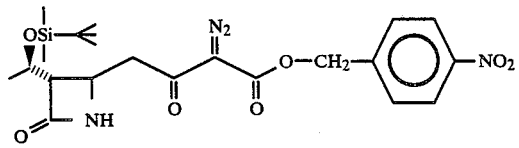

(3S,4R)-3-[(1R)-1-tert.-Butyldimethylsilyloxyethyl]-4-[3-diazo-3-p-nitrobenzyloxycarbonyl-2-oxopropyl]azetidin-2-one As described for Example 1, 2.02 g (82%) of the title compound were obtained as a viscous oil, Rf: 0.35 (toluene:ethyl acetate 3:2), $[\alpha]_D^{20}=44.75°$ (c 0.373, CHCl3), from 1.44 g (5.0 mmol) of (3R,4R)-4-acetoxy-3-[(1R)-t-tert.-butyldimethylsilyloxyethyl]azetidin 2-one and 1.71 g (6.5 mmol) 4-nitrobenzyl-2-diazo-3-oxobutanoate after chromatography of the crude product on 35 g of silica gel (toluene:ethyl acetate 7:3).

IR (CHCl3) 2160 (N2), 1759 (C=O, β-lactam), 1722, 1655, 1520 (NO2 as.), 1355 cm$^{-1}$ (NO2 s.).

$^1$H-NMR (250 MHz, CDCl3) δ 0.006, 0.007 (s, 6H, CH3Si), 0.86 (s, 9H, CH3C—Si), 1.22 (d, J=6 Hz, 3H, CHCH3), 2.97 (dd, J=2 Hz, 5 Hz, 1H, H-3), 3.01 (dd, J=10 Hz, 17 Hz, 1H, CH2CO), 3.41 (dd, J=3 Hz, 17 Hz, 1H, CH2CO), 4.04 (m, 1H, H-4), 4.20 (dq, J=5 Hz, 6 Hz, 1H, CH2CH), 5.38 (s, 2H, COOCH2) 7.57 and 8.28 (d, J=9 Hz, each 2H, p-NO2—C6H4).

EXAMPLE 3

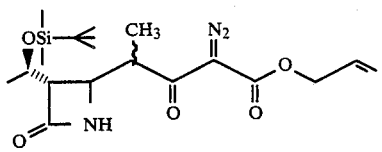

(3S,4R)-3-[(1R)-1-tert.-Butyldimethylsilyloxyethyl]-4-[(1R,S)-3-allyloxycarbonyl-3-diazo-1-methyl-2-oxopropyl]-azetidin-2-one 1.8 ml (13.0 mmol - 3 equivalents) of triethylamine were added to a solution, which had been cooled to 0° C., of 1.23 g (4.28 mmol) of (3R,4R)-4-acetoxy-3-[(1R)-1-tert.-butyldimethylsilyloxyethyl]azetidin-2-one and 1.18 g (6.5 mmol - 1.5 equivalents) of allyl 2-diazo-3-oxopentanoate in 48 ml of anhydrous dichloromethane, and then 2.3 ml (12 mmol - 2.8 equivalents) of trimethylsilyl trifluoromethanesulphonate were added dropwise. The cooling bath was removed, the mixture was stirred at room temperature for 4 h, 0.4 ml (2.0 mmol - 0.5 equivalent) of trimethylsilyl trifluoromethanesulphonate was added, and the mixture was stirred at room temperature for a further 1 h. Then the reaction solution was poured into a mixture of cold, saturated NaHCO3 solution and ethyl acetate, extraction with ethyl acetate was carried out, followed by washing with saturated NaCl solution and drying over MgSO4. The solvent was evaporated in vacuo, and the residue was chromatographed on 60 g of silica gel (toluene:ethyl acetate 4:1). 870 mg (42%) of the title compound were obtained as a 6:4 mixture of the (1R,S)-1-methyl diastereomers as pale crystals, melting point: 167° C., Rf: 0.21 (toluene-:ethyl acetate 4:1).

IR (KBr) 2135 (N2), 1761 (C=O, β-lactam), 1720 (C=O), 1657 cm$^{-1}$.

$^1$H-NMR (250 MHz, CDCl3) δ 0.07, 0.08 (s, 6H, CH3Si), 0.86, 0.87 (s, 9H, CH3C—Si), 1.18, 1.20 (d, J=7 Hz, 3H, CH3CH), 1.22, 1.26 (d, J=7.5 Hz, 3H, CH3CHOSi), 2.82, 2.98 (dd, J=2 Hz, 5Hz, 1H, H-3), 3.58 3.90 (m, 1H, CH3CH), 3.92 (m, 1H, H-4), 4.20 (m, 1H, CH3CHOSi), 4.75 (m, 2H, CH2—CH=CH2), 5.3–5.4 (m, 2H, CH=CH2), 5.81, 5.91 (bs, 1H, NH), 5.9–6.1 (m, 1H, —CH2—CH=CH2).

EXAMPLE 4

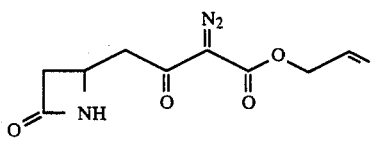

4-(3-Allyloxycarbonyl-3-diazo-2-oxopropyl)azetidine-2-one

As described for Example 1, 3.60 g (76%) of the title compound were obtained as pale crystals, melting point: 83° C., Rf: 0.26 (toluene:ethyl acetate 1:4), from 2.58 g (20.0 mmol) of 4-acetoxy-2-azetidinone [German Patent Specification No. 1,906,401 - 08.02.1969] and chromatography of the crude product on 200 g of silica gel (toluene:ethyl acetate 1:3).

IR (KBr) 2150 (N$_2$), 1771 (C=O, β-lactam), 1701, 1634 cm$^{-1}$.

$^1$H-NMR (250 MHz, CDCl$_3$) δ 2.69 (dd, J=1 Hz, 14.5 Hz, 1H, H-3β), 3.04 (dd, J=10 Hz, 18 Hz, 1H, CH$_2$CO), 3.19 (ddd, J=1 Hz, 5 Hz, 14.5 Hz, 1H, H-3α), 3.40 (dd, J=5 Hz, 18 Hz, 1H, CH$_2$CO), 4.01 (m, 1H, H-4), 4.76 (m, 2H, CH$_2$—CH=CH$_2$), 5.3-5.4 (m, 2H, —CH=CH$_2$), 5.9-6.1 (m, 1H, CH$_2$—CH=CH$_2$), 6.10 (bs, 1H, NH).

C$_{10}$H$_{11}$N$_3$O$_4$ (237.2): calculated: C 50.63, H 4.67, N 17.71. found: C 50.2, H 4.7, N 16.8.

EXAMPLE 5

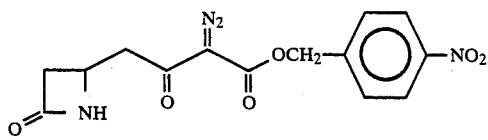

4-(3-Diazo-3-p-nitrobenzyloxycarbonyl-2-oxopropyl)azetidin-2-one (a) As described for Example 1, 1.12 g (67%) of the title compound is obtained as colorless crystals, melting point: 104° C., Rf: 0.29 (ethyl acetate), from 646 mg (5.0 mmol) of 4-acetoxy-2-azetidinone and 1.71 g (6.5 mmol) of 4-nitrobenzyl 2-diazo-3-oxobutanoate and chromatography of the crude product on 27 g of silica gel (toluene:ethyl acetate 3:2).

IR (KBr) 2145 (N$_2$), 1767 (C=O, β-lactam, 1969, 1653, 1528 (NO$_2$ as.), 1349 cm$^{-1}$ (NO$_2$ s.).

$^1$H-NMR (250 MHz, CDCl$_3$) δ 2.70 (dd, J=1 Hz, 17.5 Hz, 1H, H-3β), 3.08 (dd, J=9.5 Hz, 18 Hz, 1H, CH$_2$CO), 3.20 (ddd, J=1.5 Hz, 5 Hz, 17.5 Hz, 1H, H-3α), 3.40 (dd, J=5 Hz, 18 Hz, 1H, CH$_2$CO), 4.04 (m, 1H, H-4), 5.42 (s, 2H, COOCH$_2$), 7.59 and 8.42 (d, J=10 Hz, each 2H, p-NO$_2$—C$_6$H$_4$)

C$_{14}$H$_{12}$N$_4$O$_6$ (332.3): calculated: C 50.61, H 3.64, N 16.86. found: C 3.6, N 16.7.

(b) 2.32 ml (13.0 mmol) of ethyldiisopropylamine and then 2.3 ml (12 mmol) of trimethylsilyl trifluoromethanesulphonate were added to a solution, which had been cooled to 0° C., of 646 mg (5.0 mmol) of 4-acetoxy-2-azetidinone and 1.71 g (6.5 mmol) of 4-nitrobenzyl 2-diazo-3-oxobutanoate in 48 ml of anhydrous THF. The cooling bath was removed and the mixture was stirred at room temperature for 1 h, then 0.3 ml (1.5 mmol) of trimethylsilyl trifluoromethanesulphonate was added, and the mixture was stirred at room temperature for 1 h and worked up as described in Example 1. After chromatography of the crude product on 90 g of silica gel (ethyl acetate), 950 mg (57%) of the title compound were obtained as colorless crystals, melting point 103°-104° C. The other physical data were identical to those of the substance obtained by method (a).

EXAMPLE 6

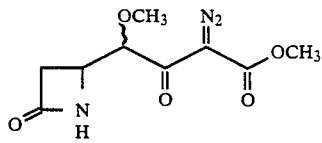

4-(3-Diazo-1-methoxy-3-methoxycarbonyl-2-oxopropyl)azetidin-2-one

As described for Example 1, the title compound was obtained as a 5:1 mixture of diastereomers which could not be separated, Rf: 0.19 (toluene:ethyl acetate 1:9), from 646 mg (5.0 mmol) of 4-acetoxy-2-azetidinone and 1.12 g (6.5 mmol) of methyl 2-diazo-4-methoxy-3-oxobutanoate after 4 h at room temperature and chromatography of the crude product on 60 g of silica gel (toluene:ethyl acetate 1:9).

IR (CHCl$_3$) 2150 (N$_2$), 1560 (C=O), β-lactam 1720 1660 cm$^{-1}$.

$^1$H-NMR (250 MHz, CDCl$_3$), predominant diastereomer δ 2.93 (dd, J=4.5 Hz, 15 Hz, 1H, H-3), 3.07 (dd, J=1.5 Hz, 15 Hz, 1H, H-3β), 3.46 (s, 3H, OCH$_3$), 3.90 (s, 3H, COOCH$_3$), 3.95 (m, 1H, H-4), 4.90 (d, J=4.5 Hz, 1H, CH—CH—OCH$_3$), 6.00 (bs, 1H, NH).

EXAMPLE 7

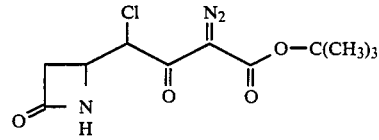

4-(3-tert.-Butyloxycarbonyl-1-chloro-3-diazo-2-oxopropyl)azetidin-2-one 1.8 ml (13.0 mmol - 2.6 equivalents) of triethylamine and then 2.3 ml (12.0 mmol - 2.4 equivalents) of trimethylsilyl trifluoromethanesulphonate were added to a solution, which had been cooled to 0° C., of 646 mg (5.0 mmol) of 4-acetoxy-2-azetidinone and 1.42 g (6.5 mmol) of tert.-butyl 4-chloro-2-diazo-3-oxobutanoate in 45 ml of anhydrous dichloromethane. The cooling bath was removed and the mixture was stirred at room temperature for 5 h, then 0.3 ml (1.5 mmol - 0.3 equivalent) of trimethylsilyl trifluoromethanesulphonate was added and the mixture was stirred at room temperature for 1 h. To work up, it was poured into a mixture of cold saturated NaHCO$_3$ solution and ethyl acetate, extraction with ethyl acetate was carried out, and the organic extracts were washed with saturated NaCl solution and dried over MgSO$_4$. After evaporation of the solvent in vacuo and chromatography on 40 g of silica gel (toluene:ethyl acetate 1:1), 426 mg (30%) of the title compound were obtained as a mixture of diastereomers (10:1), Rf: 0.35 (toluene:ethyl acetate 1:1).

IR (CHCl₃) 3419 (NH), 2143 (N₂), 1770 (C=O, β-lactam), 1711, 1648 cm⁻¹.

¹H-NMR (250 MHz, CDCl₃) δ 1.56 (s, 9H, C(CH₃)₃), 2.95 (dd, J=1.5 Hz, 15 Hz, 1H, H-3β, 3.24 (ddd, J=2.5 Hz, 5 Hz, 15.5 Hz, 1H, H-3α), 4.15 (m, 1H, H-4), 5.20 (d, J=9 Hz, 1H, CH—CHCl), 6.05 (bs, 1H, NH).

C₁₁H₁₄ClN₃O₄ (287.7): calculated: C 45.92, H 4.91. found: C 46.2, H 5.1.

EXAMPLE 8

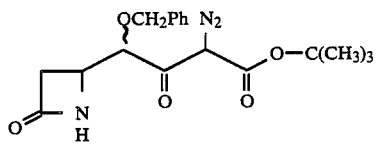

4-(1-Benzyloxy-3-tert.-butoxycarbonyloxy-3-diazo-2-oxopropyl)azetidin-2-one

As described for Example 7, the title compound was obtained as a mixture of the two diastereomers in the ratio >9:1, Rf: 0.56 (toluene:ethyl acetate 1:9), from 646 mg (5.0 mmol) of 4-acetoxy-2-azetidinone and 1.89 g (6.5 mmol) of tert.-butyl 4-benzyloxy-2-diazo-3-oxobutenoate and chromatography of the crude product on 150 g of silica gel.

IR (CHCl₃) 2145 (N₂), 1765 (C=O, β-lactam), 1705, 1650 cm⁻¹.

¹H-NMR (250 MHz, CDCl₃) δ 1.50 (s, 9H, C(CH₃)₃), 2.90 ddd, J=2 Hz, 5 Hz, 16 Hz, 1H, H-3α), 3.09 (dd, J=1 Hz, 16 Hz, 1H, H-3β), 3.92 (m, 1H, H-4), 4.48, 4.72 (AB, J=11 Hz, 2H, OCH₂Ph), 5.08 (d, J=4.5 Hz, 1H, CHCHOCH₂Ph), 6.03 (bs, 1H, NH).

EXAMPLE 9

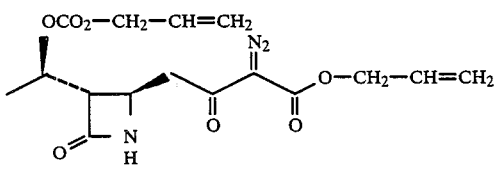

(3s,4R)-3-[(1R)-1-Allyloxycarbonyloxyethyl]-4-[3-allyloxycarbonyl-3-diazo-2-oxopropyl]azetidin-2-one As described for Example 1, 226 mg (36%) of the title compound were obtained as an oil, Rf: 0.26 (toluene:ethyl acetate 3:2), from 447 mg (1.74 mmol) of (3R,4R)-4-acetoxy-3-[(1R)-1-allyloxycarbonyloxyethyl]azetidin-2-one and 380 mg (2.26 mmol) of allyl 2-diazo-3-oxobutanoate after chromatography of the crude product on 30 g of silica gel (toluene:ethyl acetate 3:2).

IR (CHCl₃) 2150 (N₂), 1755 (C=O, β-lactam), 1720 1645 cm⁻¹.

¹H-NMR (250 MHz, CDCl₃) δ 1.44 (d, J=6.5 Hz, 3H, CH₃CH), 3.03 (dd, J=9.5 Hz, 18 Hz, CH₂CO), 3.08 (m, H-6) together 2H, 3.44 (dd, J=4.5 Hz, 18 Hz, 1H, CH₂CO), 4.0 (m, 1H, H-5), 4.62 (m, 2H, —CH₂—CH=CH₂), 4.74 (m, 2H, —CH₂—CH=CH₂), 5.11 (dq, J=6.5 Hz, 7 Hz, 1H, CH₃CHO), 5.25-5.4 (m, 4H, CH=CH₂), 5.9-6.0 (m, 2H, CH=CH₂), 6.14 (bs, 1H, NH).

EXAMPLE 10

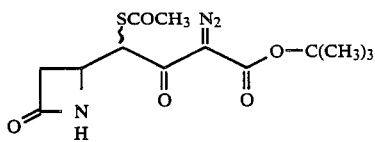

4-(1-Acetylthio-3-tert.-butoxycarbonyl-3-diazo-2-oxopropyl)-azetidin-2-one

As described for Example 7, 348 mg (21%) of the title compound were obtained as a mixture of the two diastereomers in the ratio 2:1, Rf: 0.22 (toluene:ethyl acetate 3:2), from 646 mg (5.0 mmol) of 4-acetoxy-2-azetidinone and 1.67 g (6.5 mmol) of tert.-butyl 4-acetylthio-2-diazo-3-oxobutanoate and chromatography of the crude product on 50 g of silica gel (toluene:ethyl acetate 3:2).

IR (CHCl₃) 2140 (N₂), 1765 (C=O, β-lactam), 1713 1641 cm⁻¹.

¹H-NMR (250 MHz, CDCl₃) δ 1.52, 1.53 (s, 9H, C(CH₃)₃), 2.38 (s, 3H, COCH₃), 2.7-3.1 (m, 2H, H-3, H-3'), 4.10 (m, 1H, H-4), 5.45 (d, J=6 Hz), 5.58 (d, J=5 Hz, CH—CHSCOCH₃ together 1 H, 5.92, 6.10 (bs, 1H, NH).

EXAMPLE 11

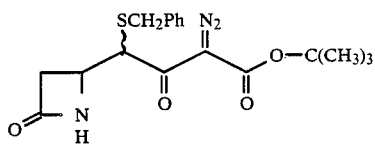

4-(1-Benzylthio-3-tert.-butoxycarbonyl-3-diazo-2-oxopropyl)-azetidin-2-one

As described for Example 7, 410 mg (22%) of the title compound were obtained as a mixture of the two diastereomers in the ratio 3:1, crystals, melting point: 119° C., Rf: 0.31 (toluene:ethyl acetate 3:2), from 646 mg (5.0 mmol) of 4-acetoxy-2-azetidinone and 1.99 g (6.5 mmol) of tert.-butyl 4-benzylthio-2-diazo-3-oxobutanoate after chromatography of the crude product on 180 g of silica gel (toluene:ethyl acetate 3:2).

IR (CHCl₃) 2140 (N₂), 1758 (C=O, β-lactam), 1705, 1632 cm⁻¹.

¹H-NMR (250 MHz, CDCl₃) δ 1.56, 1.57 (s, 9H, C(CH₃)₃), 2.52 (dd, J=15 Hz, 1.5 Hz, 1H, 3-Hβ), 2.92 (ddd, J=15 Hz, 4.5 Hz, 3 Hz, 1H, 3-H), 3.78, 3.89 (AB, J=14.5 Hz, 2H, SCH₂Ph), 4.0 (m, 1H, H-4), 4.47 (d, J=10 Hz, CHSCH₂Ph), 4.63 (d, J=8 Hz, CHSCH₂Ph), together 1H, 5.62, 5.70 (bs, 1H, NH), 7.4 (m, 5H, Ph).

C₁₈H₂₁N₃O₄S: calculated: C 57.58, H 5.64, N 11.19, S 8.54, found: C 57.2, H 5.6, N 10.7, S 8.7,

EXAMPLE 12

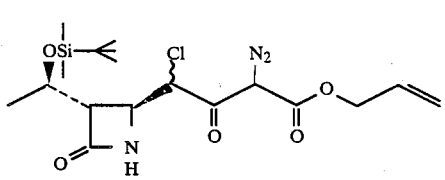

(3S,4S)-3-[(1R)-1-tert.-Butyldimethylsilyloxyethyl]-4-[[1R)-3-allyloxycarbonyl-1-chloro-3-diazo-2-oxo-propyl]-azetidin-2-one and (3S,4S)-3-[(1R)-1-tert.-Butyldimethylsilyloxyethyl]-4-[(1S)-3-allyloxycarbonyl-1-chloro-3-diazo-2-oxopropyl]-azetidin-2-one As described for Example 7, 171 mg (8%) of the unpolar isomer are obtained as colorless crystals, melting point: 104° C., Rf: 0.38 (toluene:ethyl acetate 4:1), from 1.44 g (5.0 mmol) of (3R,4R)-4-acetoxy-3-[(1R)-1-tert.-butyldimethylsilyloxyethyl]azetidin-2-one and 1.32 g (6.5 mmol) of ally 4-chloro-2-diazo-3-oxobutanoate and chromatography of the crude product on 240 g of silica gel (toluene:ethyl acetate 85:15).

IR (KBr) 2145 ($N_2$), 1769 (C=O, β-lactam), 1720, 1662 cm$^{-1}$.

$^1$H-NMR (300 MHz, CDCl$_3$) δ 0.08 (s, 6H, CH$_3$Si), 0.87 (s, 9H, CH$_3$C-Si), 1.20 (d, J=6.3 Hz, 3H, CH$_3$CH), 3.07 (m, 1H, H-3), 4.08 (dd, J=2.3 Hz, 4.3 Hz, 1H, H-4), 4.17 (dq, J=3.8 Hz, 6.3 Hz, 1H, CH$_3$CHOSi), 4.70 (d, J=5.8 Hz, 2H, CH$_2$—CH=CH$_2$), 5.3–5.4 (m, 2H, CH=CH$_2$), 5.50 (d, J=4.3 Hz, 1H, CHCl), 5.8–6.0 (m, 1H, —CH$_2$—CH=CH$_2$), 6.0 (bs, 1H, NH).

In addition, 755 mg (35%) of the polar isomer were obtained as colorless crystals, melting point: 107° C., Rf: 0.27 (toluene:ethyl acetate 4:1).

IR (K8r) 2140 ($N_2$), 1768 (C=O, β-lactam), 1720, 1671 cm$^{-1}$.

$^1$H-NMR (300 MHz, CDCl$_3$) δ 0.08, 0.09 (s, 6H, CH$_3$Si), 0.88 (s, 9H, CH$_3$C-Si), 1.24 (d, J=6.3 Hz, 3H, CH$_3$CH), 3.08 (dd, J=2.3 Hz, 2.4 Hz, 1H, H-3), 4.26 (dd, J=2 Hz, 8.9 Hz, H-4), 4.3 (m, CH$_3$CHOSi) together 2H, 4.79 (m, 2H, CH$_2$—CH=CH$_2$), 5.20 (d, J=8.9 Hz, 1H, CHCl), 5.3–5.4 (m, 2H, CH=CH$_2$), 5.86 (bs, NH), 5.8–6.0 (m, —CH$_2$—CH=CH$_2$) together 2H.

EXAMPLE 13

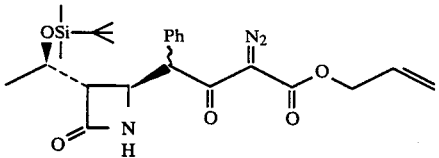

(3S,4R)-3-[(1R)-1-tert.-Butyldimethylsilyloxyethyl]-4-[(1R)-allyloxycarbonyl-3-diazo-2-oxo-1-phenyl-propyl]-azetidin-2-one and (3S,4R)-3-[1R)-1-tert.-Butyldimethylsilyloxyethyl]-4-[(1S)-3-allyloxycarbonyl-3-diazo-2-oxo-1-phenyl-propyl]-azetidin-2-one As described for Example 7, 200 mg (9%) of the unpolar title compound are obtained as an oil, Rf: 0.32 (toluene:ethyl acetate 4:1), from 1.44 g (5.0 mmol) of (3R,4R)-4-acetoxy-3-[(1R)-1-tert.-butyldimethylsilyloxyethyl]-azetidin-2-one and 1.59 g (6.5 mmol) of allyl 2-diazo-3-oxo-4-phenylbutanoate and chromatography of the crude product on 230 g of silica gel (toluene:ethyl acetate 4:1).

IR (CHCl$_3$) 2140 ($N_2$), 1760 (C=O, β-lactam), 1720, 1650 cm$^{-1}$.

$^1$H-NMR (300 MHz, CDCl$_3$) δ 0.07, 0.08 (s, 6H, CH$_3$Si), 0.88 (s, 9H, CH$_3$C-Si), 1.19 (d, J=6.3 Hz, 3H, CH$_3$CH), 2.68 (m, 1H, H-3), 4.18 (m, CH$_3$CHOSi), 4.24 (dd, J=2.5 Hz, 6.5 Hz, H-4) together 2H, 4.6–4.8 (m, 2H, CH$_2$—CH=CH$_2$), 4.97 (d, J=6.5 Hz, 1H, CHPh), 5.2–5.4 (m, 2H, CH=CH$_2$), 5.83 (bs, NH), 5.8–6.0 (m, CH$_2$—CH=CH$_2$) together 2H, 7.35 (m, 5H, Ph).

In addition, 530 mg (22%) of the polar title compound were obtained as colorless crystals, melting point: 139° C., Rf: 0.21 (toluene:ethyl acetate 4:1).

IR (KBr) 2138 ($N_2$), 1764 (C=O, β-lactame), 1725, 1658 cm$^{-1}$.

$^1$H-NMR (300 MHz, CDCl$_3$) δ 0.01 (s, 6H, CH$_3$Si), 0.25 (d, J=6 Hz, 3H, CH$_3$CH), 0.88 (s, 9H, CH$_3$C-Si), 2.84 (m, 1H, H-3), 4.09 (m, 1H, CH$_3$CHOSi), 4.36 (dd, J=2.3 Hz, 10.5 Hz, H-4), 4.66 (m, —CH$_2$—CH=CH$_2$), 4.73 (d, J=10.5 Hz, CHPh) together 2H, 5.2–5.4 (m, 2H, CH=CH$_2$), 5.9–6.0 (m, CH$_2$—CH=CH$_2$), 5.94 (bs, NH) together 2H, 7.34 (m, 5H, Ph).

EXAMPLE 14

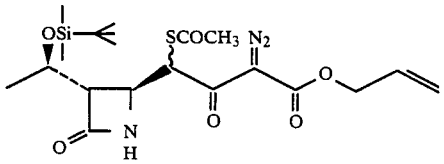

(3S,4S)-3-[(1R)-1-tert.-Butyldimethylsilyloxyethyl]-4-[(1R)-1-acetylthio-3-allyloxycarbonyl-3-diazo-2-oxo-propyl]azetidin-2-one and (3S,4S)-3-[(1R)-1-tert.-Butyldimethylsilyloxyethyl]-4-[(1S)-1-acetylthio-3-allyloxycarbonyl-3-diazo-2oxo-propyl]azetidin-2-one As described for Example 7, 457 mg (15%) of the unpolar title compound were obtained as an oil, Rf: 0.40 (toluene:ethyl acetate 7:3), from 2.70 g (9.4 mmol) of (3R,4R)-4-acetoxy-3-[(1R)-1-tert.-butyldimethylsilyloxyethyl]azetidin-2-one and 2.96 g (12.2 mmol) of allyl 4-acetylthio-2-diazo-3-oxobutanoate and chromatography of the crude product on 650 g of silica gel (toluene:ethyl acetate 4:1).

IR (CHCl$_3$) 2135 ($N_2$), 1765 (C=O, β-lactam), 1715, 1638 cm$^{-1}$.

$^1$H-NMR (250 MHz, CDCl$_3$) δ 0.07, 0.08 (s, 6H, CH$_3$Si), 0.87 (s, 9H, CH$_3$c—Si), 1.22 (d, J=6.5 Hz, 3H, CH$_3$CH), 2.39 (s, 3H, SCOCH$_2$), 2.92 (m, 1H, H-3), 4.18 (m, H-4), 4.23 (m, CH$_3$CHOSi) together 2H, 4.75 (m, 2H, —CH$_2$—CH=CH$_2$), 5.3–5.4 (m, CH=CH$_2$), 5.61 (d, J=4 Hz, 1H, CHSCOCH$_3$), 5.8–6.0 (m, —CH$_2$—CH=CH$_2$), 5.98 (bs, NH) together 2H.

In addition, 1.5 g (48%) of the polar title compound was obtained as an oil, Rf: 0.36 (toluene:ethyl acetate 7:3).

IR (CHCl$_3$) 3350 (NH), 2140 ($N_2$), 1758 (C=O, β-lactam), 1715, 1640 cm$^{-1}$.

$^1$H-NMR (250 MHz, CDCl$_3$) δ 0.07 (s, 6H, CH$_3$Si), 0.88 (s, 9H, CH$_3$C-Si), 1.19 (d, J=6.5 Hz, 3H, CH$_3$CH), 2.37 (s, 3H, SCOCH$_3$), 3.12 (m, 1H, H-3), 4.20 (dd, J=2 Hz, 7.5 Hz, H-4), 4.20 (m, CH$_3$CHOSi) together 2H, 4.75 (m, 2H, —CH$_2$—CH=CH$_2$), 5.3–5.4 (m, 2H, —CH=CH$_2$), 5.42 (d, J=7.5 Hz, 1H, CHSCOCH$_3$), 5.80 (bs, 1H, NH), 5.85–6.0 (m, 1H, CH$_2$—CH=CH$_2$).

EXAMPLE 15

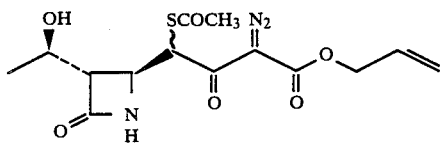

(3S,4S)-3-[(1R)-1-Hydroxyethyl]-4-[(1R,S)-1-acetylthio-3-allyloxycarbonyl-3-diazo-2-oxopropyl]azetidin-2-one 1.15 ml (8.3 mmol - 3.6 equivalents) of triethylamine and then 1.51 ml (7.8 mmol - 3.4 equivalents) of trimethylsilyl trifluoromethanesulphonate were added to a solution, which had been cooled to 0° C., of 400 mg (2.3 mmol) of (3R,4R)-4-acetoxy-3-[(1R)-1-hydroxyethyl]-]azetidin-2-one and 720 mg (3.0 mmol) of allyl 4-acetylthio-2-diazo-3-oxobutanoate in 20 ml of anhydrous dichloromethane. The cooling bath was removed, the mixture was stirred at room temperature for 4 h, 133 μl (0.7 mmol - 0.3 equivalent) of trimethylsilyl trifluoromethanesulphonate were added, and the mixture was stirred at room temperature for 3 h and worked up as described in Example 1. After chromatography of the crude product on 40 g of silica gel (ethyl acetate), the title compound was obtained as a mixture of the two diastereomers which could not be separated, Rf: 0.31 (ethyl acetate).

IR (CHCl$_3$) 3380 (NH), 2150 (N$_2$), 1758 (C=O, β-lactam), 1720, 1642 cm$^{-1}$.

$^1$H-NMR (250 MHz, CDCl$_3$) δ1.30, 1.32 (d, J=6.3 Hz, 3H, CH$_3$CH), 2.25, 2.75 (bs, 1H, OH), 2.40 (s, 3H, SCOCH$_3$), 2.96, 3.14 (m, 1H, H-3), 4.14 (m, 2H, H-4, CH$_3$CHOH), 5.25 (m, 2H, CH$_2$—CH=CH$_2$), 5.3–5.4 (m, 2H, CH=CH$_2$), 5.50 (d, J=6Hz, CHSCOCH$_3$), 5.45 (d, J=4.8 Hz, CHSCOCH$_3$) together 1H, 5.85–6.05 (m, 1H, CH$_2$—CH=CH$_2$), 6.15 (bs, 1H, NH).

EXAMPLE 16

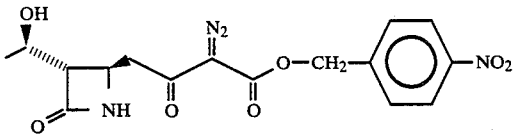

(3S,4S)-3-[(1R)-1-Hydroxyethyl]-4-[3-diazo-3-p-nitrobenzyl-oxycarbonyl-2-oxopropyl]azetidin-2-one 10 mg (0.02 mmol) of (3S,4R)-3-[(1R)-1-tert.-butyldimethylsilyloxyethyl]-4-[3-p-nitrobenzyloxycarbonyl-2-oxopropyl]azetidin-2-one were dissolved, at 0° C., in 1 ml of a standard solution of 3.76 μl (0.03 mmol - 1.5 equivalents) of boron trifluoride etherate in acetonitrile, and the mixture was stirred at this temperature for 2 h. The reaction solution was then filtered through 0.5 g of silica gel/NaHCO$_3$ and evaporated in vacuo, and the title compound was obtained, Rf: 0.24 (toluene:ethyl acetate 1:9).

IR (CHCl$_3$) 3419 (OH), 2142 (N$_2$), 1768 cm$^{-1}$ (C=O, β-lactam).

$^1$H-NMR (250 MHz, CDCl$_3$) δ1.35 (d, J=6.5 Hz, 3H, CH$_3$CH), 1.62 (bs, 1H, OH), 2.91 (dd, J=1.5 Hz, 7.5 Hz, 1H, H-6), 3.22 (dd, J=7.5 Hz, 19 Hz, 1H, CH$_2$CO), 3.35 (dd, J=7.5 Hz, 19 Hz, 1H, CH$_2$CO), 4.00 (m, 1H, H-5), 4.20 (dq, J=6.5 Hz, 7.5 Hz, 1H, CH$_3$CHOH), 5.40 (s, 2H, COOCH$_2$), 6.00 (bs, 1H, NH), 7.58 and 8.30 (d, J=9 Hz, each 2H, p—NO$_2$—C$_6$H$_4$).

The compound of this example has been used as an intermediate for the synthesis of thienamycin [U.S. Pat. No. 4,290,947: Th. N. Salzmann et al. J. Am. Chem. Soc. 102 6163 (1980)].

PREPARATION EXAMPLE 17

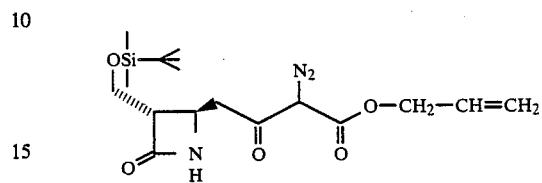

(3S,4R)-3-tert.-Butyldimethylsilyloxymethyl]-4-[3-allyloxycarbonyl-3-diazo-2-oxopropyl]azetidin-2-one 0.72 ml (5.2 mmol) of triethylamine and then, dropwise, 0.93 ml (4.8 mmol) of trimethylsilyl trifluoromethanesulphonate were added to a solution, which had been cooled to 0° C., of 547 mg (2.0 mmol) of (3R,4R)-4-acetoxy-3-[tert.-butyldimethylsilyloxymethyl]azetidin-2-one and 437 mg (2.6 mmol) of allyl 2-diazo-3-oxobutanoate in 18 ml of anhydrous dichloromethane. The cooling bath was removed, the mixture was stirred at room temperature for 15 min, 0.12 ml (0.6 mmol) of trimethylsilyl trifluoromethanesulphonate was added, and the mixture was stirred at room temperature for a further 15 min. The reaction solution was then poured into a mixture of cold, saturated NaHCO$_3$ solution and ethyl acetate, extraction with ethyl acetate was carried out, and the organic extracts were washed with saturated NaCl solution and dried over MgSO$_4$. The solvent was evaporated in vacuo and the residue was chromatographed on 50 g of silica gel (toluene:ethyl acetate 4:1). 462 mg (61%) of the title compound were obtained as an oil, Rf: 0.11 (toluene:ethyl acetate 4:1).

IR (CHCl$_3$) 3380 (NH), 2150 (N$_2$), 1760 (C=O, β-lactam), 1715, 1648 cm$^{-1}$.

$^1$H-NMR (250 MHz, CDCl$_3$) δ0.07 (s, 6H, CH$_3$Si), 0.88 (s, 9H, CH$_3$CSi), 3.03 (m, 1H, H-3), 3.11 (dd, J=10 Hz, 18 Hz, 1H, CH$_2$CO), 3.40 (dd, J=5 Hz, 18 Hz, 1H, CH$_2$CO), 3.95 (m, H-4), 4.0 (m, CH$_2$OSi) together 3H, 4.76 (m, 2H, CH$_2$—CH=CH$_2$), 5.3–5.45 (m, 2H, —CH=CH$_2$), 5.9–6.1 (m, —CH$_2$—CH=CH$_2$), 6.01 (bs, NH) together 2H.

EXAMPLE 18

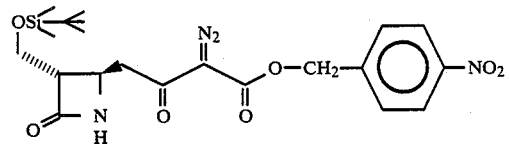

(3S,4R)-3-[tert.-Butyldimethylsilyloxymethyl]-4-[3-diazo-3-p-nitrobenzyloxycarbonyl-2-oxopropyl]azetidin-2-one As described for Example 17, 1.22 g (65%) of the title compound were obtained as colorless crystals, melting point: 104° C., Rf: 0.31 (toluene:ethyl acetate 1:1), from 930 mg (3.4 mmol) of (3R,4R)-4-acetoxy-3-[tert.-butyldimethylsilyloxymethyl]azetidin-2-one and 1.16 g (4.42 mmol - 1.3 equivalents) of 4-nitrobenzyl 2-diazo-3-oxobutanoate after chromatography of the crude product on 100 g of silica gel (toluene:ethyl acetate 1:1).

IR (KBr) 3352 (NH), 2139 ($N_2$), 1755 (C=O, β-lactam), 1713, 1660, 1525 ($NO_2$ as.), 1349 cm$^{-1}$ ($NO_2$ s.).

$^1$H-NMR (300 MHz, CDCl$_3$) δ0.06 (s, 6H, CH$_3$Si), 0.86 (s, 9H, CH$_3$CSi), 2.98 (m, 1H, H-3), 3.05 (dd, J=9 Hz, 18 Hz, 1H, CH$_2$CO), 3.34 (dd, J=5 Hz, 1H, CH$_2$CO), 3.89 (m, 1H, H-4), 3.96 (m, 2H, CH$_2$OSi), 5.31 (s, 2H, COOCH$_2$), 5.93 (bs, 1H, NH), 7.50 (d, J=9 Hz, 2H, H$_{arom.}$), 8.23 (d, J=9 Hz, 2H, H$_{arom.}$).

As described in Example 7, the following compounds (Example 19-24, Table 3) were obtained by reaction of (3R,4R)-4-acetoxy-3-[(1R)-1-tert.-butyldimethylsilyloxyethyl]azetidin-2-one with the corresponding diazoacetoacetic esters:

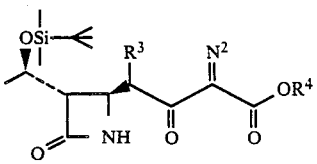

(The time column represents the stirring time at room temperature after addition of the catalytic amount of trimethylsilyl trifluoromethanesulphonate).

TABLE 3

| Example No. | R³ | R⁴ | Time (h) | Rf (Tol.:Ethylac.) | IR (cm⁻¹) | ¹H—NMR (250 MHz, CDCl₃) δ ppm | Notes |
|---|---|---|---|---|---|---|---|
| 19 | SCH | CH₂—CH=CH₂ | 2 | 0.14, 0.18 (4:1) | 3416 (NH) 2155 (N₂) 1775 (C=O) 1714 1652 | 0.08 (s, 6H, CH₂Si), 0.88 (s, 9H, CH₂C—Si), 1.23, 1.30 (d, J=6.3 Hs, 3H, CH₂CH), 3.0–3.2 (m, 1H, N—3), 4.25–4.45 (m, 2H, CH₂CHO, N—4), 4.68 (d, J=10 Hz, CHSCN), 5.19 (d, J=5.5 Hz, CHSCN), together 1N, 4.81 (m, 2H, CH₂—CH=CH₂), 5.4–5.5 (m, 2H, CH=CH₂), 5.9–6.1 (m, 1H, CH₂—CH=CH₂), 6.18, 6.60 (bs, 1H, NH). | C₁₉H₂₀N₄O₃SSi (452.61) calc: C 50.42 N 6.24 N 12.38 S 7.08 fd: C 50.5 N 6.3 N 12.4 S 7.0 diastereomers about 3:2 |
| 20 | N₂ | CH₂—CH=CH₂ | 2 | 0.25 (4:1) | 3395 (NH) 2130 (N₂) 2115 (N₂) 1762 (C=O) 1718 1658 | 0.08, 0.09 (s, 6H, CH₂Si), 0.89 (s, 9H, CH₂C—Si), 1.23 (d, J=6.5 Hz, 3H, CH₂CH), 3.14 (m, 1H, H—3), 4.13 (dd, J=2Hz, 9Hz, 1H, H—4), 4.30 (m, 1H, CH₂CHO), 4.80 (m, 2H, CH₃—CH=CH₂), 5.03 (d, J=9Hz, 1H, CHN₃), 5.4–5.5 (m, 2H, CH=CH₂), 5.77 (bs, 1H, NH), 5.9–6.1 (m, 1H, CH₂—CH=CH₂). | diastereomers about 1:1 |
| 21 | PhS | CH₂—CH=CH₂ | 7 | 0.23 (9:1) | 3380 (NH) 2140 (N₂) 1761 (C=O) 1645 | 0.07, 0.08 (s, 6H, CH₂Si), 0.88 (s, 9H, CH₂C—Si), 1.22, 1.26 (d, J=6.5Hz, 3H, CH₂CH), 3.08 (m, 1H, H—3), 4.25 (m, 2H, H—4, CH₃CHO), 4.46 (d, J=9Hz, CHSPh), 4.68 4.72 (m, 3H, CHSPh, CH₂—CH=CH₃) together 3H. 5.4–5.5 (m, 2H, CH=CH₂), 5.9–6.05 (m, 1H, CH₂—CH=CH₂), 6.08, 6.15 (bs, 1H, NH). | diastereomers |

TABLE 3-continued

| Prep. Ex. No. | R³ | R⁴ | Time (h) | (Tol:Ethylac.) | IR (cm⁻¹) | ¹H—NMR (250 MHz, CDCl₃) δ ppm | Analysis |
|---|---|---|---|---|---|---|---|
| 22 | −S−C(=N−N=N−N(CH₃)) | CH₂−CH=CH₂ | 65 0° C. | 0.29 (7:3) | 3385 (NH) 2145 (N₂) 1770 (C=O) 1718 1645 | 0.08, 0.09 (s, 6H, CH₂Si), 0.89 (s, 9H, CH₂C—Si), 1.29 (d, J=6.3Hz, 3H, CH₂CH), 3.31 (m, 1H, H—3), 3.97 (s, 3H, NCH₂), 4.43 (m, 2H, H—4, CH₃CHO), 4.75 (m, 2H, H—4, CH₂−CH=CH₂), 5.3−5.5 (m, 2H, CH=CH₂), 5.9−6.1 (m, 1H, CH₂−CH=CH₂), 6.85 (bs, 1H, NH). | Diastereomers about 8:1 |
| 23 | −P(OEt)₂ (=O) | CH₂−CH=CH₂ | 66 | 0.06 (0:1) | 3341 (NH) 2140 (N₂) 1772 (C=O) 1715 1650 1250 | 0.07, 0.08 (s, 6H, CH₂Si), 0.88 (s, 9H, CH₂C—Si), 1.24 (d, J=6Hz, 3H, CH₂CH), 3.1 (m, 1H, H—3), 4.1−4.25 (m, 2H, CH₂CHO, H—4), 4.72 (m, 2H, CH₂−CH=CH₂), 5.3 (dd, J=5Hz, 22Hz, CHP), 5.3−5.5 (m, CH=CH₂) together 3H, 5.9−6.9 (m, 1H, CH₂−CH=CH₂), 6.15 (bs, 1H, NH). | Diastereomers |
| 24 | −COO−CH₂−CH=CH₂ | CH₂−CH=CH₂ | 5.5 | 0.29, 0.25 (4:1) | 3395 (NH) 2152 (N₂) 1760 (C=O) 1720 1650 | 0.05 (s, 6H, CH₂Si), 0.86, 0.87 (s, 9H, CH₂C−Si), 1.11, 1.15 (d, J=6.5Hz, 3H, CH₂CH), 3.21, 3.24 (m, 1H, H—3). 4.24 (m, CH₂CHO) 4.34 (m, H—4) together 2H, 4.66 (d, J=7Hz, CHCOO), 4.74, 4.77 (m, CH₂−CH=CH₂) tog. 5H, 5.25−5.45 (m, 4H, CH=CH₂), 5.85−6.05 (m, CH₂−CH=CH₂), 75.92, 6.10 (bs, NH) together 3H. | Diastereomers 1:1 |

TABLE 3-continued

| | | | | | |
|---|---|---|---|---|---|
| 25 |  —CH$_2$ | 1,5 | 0.26 (7:3) | 3350 (NH)<br>2150 (N$_2$)<br>1775 (C=O)<br>1725<br>1525 (NO$_2$ as.)<br>1355 (NO$_2$ s.) | 0.06–0.08 (s, 6H, CH$_2$Si), 0.84, 0.86 (s, 9H, CH$_2$C—Si), 1.2 (m, CH$_2$CH), 1.22, 1.25 (d, J=7.5Hz, CH$_2$CHOSi) tog. 6H, 2.80, 2.96 tog. J=15Hz, 6Hz, 1H, H—3), 3.55 (m, 1H, CH$_2$CH), 3.89, 3.90 (dd, J=15Hz, 10Hz, 1H, H—4), 4.18 (m, 1H, CH$_3$CHOSi), 5.35, 5.36 (s, 2H, COOCH$_2$), 7.54 (d, J=9Hz, 2H, Harom.) 8.26 (d, J=9Hz, 2H, Harom.). | Diastereomers<br>1'(R):1'(S) = 2:3 |
| 26 | 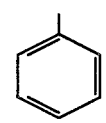 —CH$_2$ | 15 | 0.23 (7:3) | 3350 (NH)<br>2148 (N$_2$)<br>1762 (C=O)<br>1720<br>1530 (NO$_2$ as.)<br>1555 (NO$_2$ s.) | 0.01, 0.04, 0.06, 0.08 (s, 6H, CH$_2$Si), 0.25, 1.20 (d, J=6Hz, 3H, CH$_2$CHO), 0.88 (s, 9H, CH$_2$C—Si), 2.7–3.0 (m, 1H, H—3), 3.90 (m, H—4), 4.35 (dd, J=2Hz, 10Hz, H—4) tog. 1H, 4.15 (m, 1H, CH$_3$CHO), 4.68 (d, J=10Hz, PhCH), 5.18, 5.30 (d, 2H, COOCH$_2$) 5.91 5.95 (bs, 1H, NH$_2$) 7.2–7.35 (m, 5H, Ph), 7.43 (d, J=9Hz, 2H, Harom.), 8.20 (d, J=9Hz, 2H, Harom.). | Diastereomers<br>45:55 |

(C) Examples for the use of compounds of the general formula I for the preparation of carbapenem antibiotics.

EXAMPLE 1

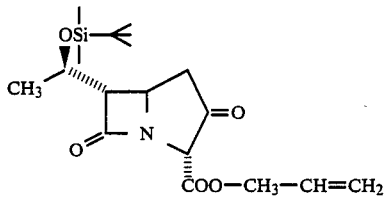

(2S,5R,6S)-2-Allyloxycarbonyl-3,7-dioxo-6-[(1R)-1-tert.-butyldimethylsilyloxyethyl]-1-azabicyclo[3.2.0-]heptane A solution of 3.96 g (10 mmol) of (3S,4R)-3-[(1R)-1-tert.-butyldimethylsilyloxyethyl]-4-[3-allyloxycarbonyl-3-diazo-2-oxopropyl]azetidin-2-one in 50 ml of anhydrous dichloromethane was heated to reflux for 30 minutes in the presence of 40 mg (1 mol-%) of rhodium-(II) acetate. The reaction solution was filtered through a little kieselguhr and silica gel and evaporated in vacuo. 3.5 g (95%) of the title compound were obtained as a colorless oil, Rf: 0.46 (toluene:ethyl acetate 7:3).

IR (CHCl$_3$) 1766, 1740 cm$^{-1}$.

$^1$H-NMR (250 MHz, CDCl$_3$) δ0.06 s, 6H, CH$_3$Si), 0.87 (s, 9H, CH$_3$C-Si), 1.26 (d, J=6.5 Hz, 3H, CH$_3$CH), 2.44 (dd, J=8 Hz, 19 Hz, 1H, CH$_2$CO), 2.88 (dd, J=8 Hz, 19 Hz, 1H, CH$_2$CO), 3.15 (dd, J=2 Hz, 1H, H-6), 4.16 (ddd, J=2 Hz, 8 Hz, 8 Hz, 1H, H-5), 4.33 (dq, J=5 Hz, 6.5 Hz, 1H, CH$_3$CH), 4.65 (m, 2H, CH$_2$—CH=CH$_2$), 4.71 (s, 1H, H-2), 5.25–5.4 (m, 2H, CH=CH$_2$), 5.8–6.0 (m, 1H, CH$_2$—CH=CH$_2$).

EXAMPLE 2

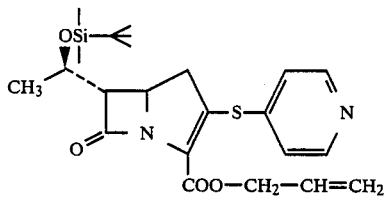

Allyl (5R,6S)-2-(4-pyridylthio)-6-[(1R)-1-tert.-butyldimethylsilyloxyethyl]carbapen-2-em-3-carboxylate 1.94 ml (13 mmol) of 1,5-diazabicyclo[5.4.0]undec-5-ene (DBU) and, after 20 minutes, 2.2 ml (13 mmol) of trifluoromethanesulphonic anhydride were added dropwise to a solution, which had been cooled to −78° C., of 3.68 g (10 mmol) of (2S,5R,6S)-2-allyloxycarbonyl-3,7-dioxo-6-[(1R)-1-tert.-butyldimethylsilyloxyethyl]-1-azabicyclo[3.2.0]heptane in 100 ml of anhydrous THF. The mixture was then stirred at −78° C. for 30 minutes and the solution was concentrated in vacuo to about 40 ml without the temperature rising above −20° C. Then, successively 20 ml of DMF, 2.1 ml (12 mmol) of ethyl diisopropylamine and 1.33 g (12 mmol) of 4-mercaptopyridine were added and the mixture was stirred at −20° C. for 1 h. The mixture was then diluted with ethyl acetate and poured into cold, saturated NaHCO$_3$ solution. Extraction was carried out with ethyl acetate, followed by washing with saturated NaCl solution and drying with MgSO$_4$. After evaporation of the solvent in vacuo and chromatography of the residue on 600 g of silica gel (toluene:ethyl acetate), 3.1 g (66%) of the title compound were obtained as a viscous oil, Rf: 0.30 (toluene:ethyl acetate 7:3).

IR (CHCl$_3$) 1781 (C=O, β-lactam), 1710 cm$^{-1}$ (C=O, ester).

$^1$H-NMR (250 MHz, CDCl$_3$) δ0.02, 0.04 (s, 6H, CH$_3$Si), 0.84 (s, 9H, CH$_3$C-Si), 1.10 (d, J=6.5 Hz, CH$_3$CH), 2.86 (dd, J=11 Hz, 18 Hz, 1H, H-1), 3.04 (dd, J=9 Hz, 18 Hz, 1H, H-1'), 3.48 (m, 1H, H-6), 4.17 (m, 2H, H-5, CH$_3$CH), 4.73 (m, 2H, CH$_2$—CH=CH), 5.25 (dd, J=1 Hz, 10.5 Hz, 1H, CH=CH$_2$—cis), 5.47 (dd, J=1 Hz, 17 Hz, 1H, CH=CH$_2$-trans), 5.9–6.1 (m, 1H, CH$_2$—CH=CH$_2$), 7.63 (d, J=5.5 Hz, 2H, 3.5-pyridyl-H), 8.62 (d, J=5.5 Hz, 2H, 2,6-pyridyl-H).

EXAMPLE 3

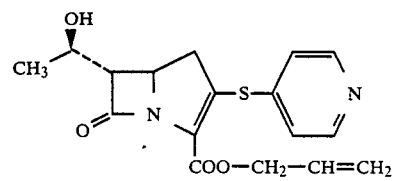

Allyl (5R,6S)-2-(4-pyridylthio)-6-[(1R)-1-hydroxyethyl]-carbapen-2-em-3-carboxylate 3.69 ml (64.5 mmol - 10 equivalents) of glacial acetic acid and 19.3 ml (19.3 mmol - 3 equivalents) of a 1M solution of tetrabutylammonium fluoride in THF were added to a solution, which had been cooled to 0° C., of 2.97 g (6.5 mmol) of allyl (5R,6S)-2-(4-pyridylthio)-6-[(1R)-1-tert.-butyldimethylsilyloxyethyl]carbapen-2-em-3-carboxylate in 60 ml of THF. The cooling bath was removed and the reaction solution was allowed to stand at room temperature for 62 h. To work up, it was poured a into a mixture of cold, saturated NaHCO$_3$ solution and ethyl acetate, extraction with ethyl acetate was carried out, followed by washing with saturated NaHCO$_3$ and NaCl solutions and drying over MgSO$_4$. After evaporation of the solvent in vacuo and chromatography of the residue on 360 g of silica gel (toluene-:ethyl acetate 9:1), 472 mg (21%) of the title compound were obtained as an oil, Rf: 0.24 (toluene:ethyl acetate 9:1).

IR (CHCl$_3$) 3400 (OH), 1776 (C=O, β-lactam) 1720 cm$^{-1}$ (C=O, ester).

$^1$H-NMR (250 MHz, CDCl$_3$) δ1.32 (d, J=6.5 Hz, 3H, CH$_3$CH), 2.78, 2.90 (dd, J=10 Hz, 18 Hz, 2H, H-1), 3.16 (dd, J=2.5 Hz, 7 Hz, 1H, H-6), 4.2 (m, 2H, H-5, CH$_3$CH), 4.75, 4.87 (dd, J=7.5 Hz, 14.5 Hz, 2H, CH$_2$—CH=CH$_2$), 5.30 (d, J=9 Hz, 1H, CH=CH$_2$-cis), 5.48 (d, J=17 Hz, 1H, CH=CH$_2$-trans), 5.9–6.1 (m, 1H, —CH$_2$—CH=CH$_2$), 7.43 (d, J=7 Hz, 2H, 3,5-pyridyl-H), 8.64 (d, J=7 Hz, 2H, 2,6-pyridyl-H).

EXAMPLE 4

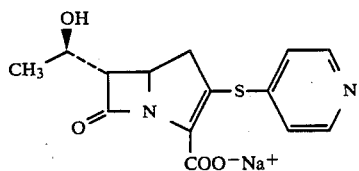

Sodium (5R,6S)-2-(4-pyridylthio)-6-[(1R)-1-hydroxyethyl]-carbapen-2-em-3-carboxylate 2.8 ml (1.4 mmol - 1.05 equivalents) of 0.5 M sodium 2-ethylhexanoate in ethyl acetate, 35 mg (0.13 mmol - 0.1 equivalent) of triphenylphosphine and 35 mg (0.03 mmol) of tetrakis-(triphenylphosphine)-palladium (0) were successively added to a solution of 462 mg (1.33 mmol) of allyl (5R,6S)-2-(4-pyridylthio)-6-[(1R)-1-hydroxyethyl]-carbapen-2-em-3-carboxylate in 3.4 ml of anhydrous dichloromethane, and the mixture was stirred at room temperature for 1 h. It was then diluted with 20 ml of anhydrous acetone. The precipitate was filtered off with suction and vigorously stirred with 50 ml of ether for 0.5 h, again filtered off with suction and dried over $P_4O_{10}$ under high vacuum. 361 mg (83%) of the title compound were obtained as a colorless hygroscopic powder.

IR (KBr) 3400 (OH), 1755 (C=0,β-lactam), 1600 (COONa), 1576, 1392 $cm^{-1}$.

$^1$H-NMR (250 MHz, DMSO) δ1.11 (d, J=6 Hz, 3H, CH$_3$CH), 2.72, 2.75 (s, 2H, H-1), 3.20 (dd, J=3 Hz, 6 Hz, 1H, H-6), 3.92 (m, 1H, H-5), 4.07 (m, 1H, CH$_3$CH), 7.33 (d, J=6 Hz, 2H, 3,5-pyridyl-H), 8.44 (d, J=6 Hz, 2H, 2,6-pyridyl-H).

It is understood that the specification and examples are illustrative but not limitative of the present invention and that other embodiments within the spirit and scope of the invention will suggest themselves to those skilled in the art.

We claim:

1. A compound of the formula

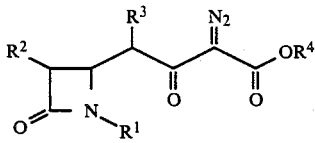

in which
$R^1$ represents hydrogen or represents an amino protective group,
$R^2$ represents hydrogen, represents halogen, represents azido or phenyl, represents $NHR^1$, represents a radical of the formula

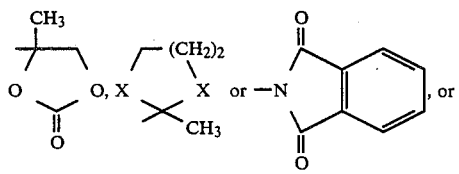

represents straight-chain, branched or cyclic, saturated or unsaturated alkyl (up to C$_6$), which is optionally substituted by fluorine, chlorine or the group O—$R^8$, X denoting sulphur or oxygen, $R^8$ representing hydrogen, representing trimethylsilyl, triethylsilyl, triisopropylsilyl, tert.-butyldimethylsilyl, triphenylsilyl, trimethylsilylethoxycarbonyl, representing benzyl, benzyloxycarbonyl, 2- or 4-nitrobenzyl, 2- or 4-nitrobenzyloxycarbonyl, tert.-butyloxycarbonyl, allyloxycarbonyl, 4-methoxybenzyl, 4-methoxybenzyloxycarbonyl, or representing formyl, acetyl, trichloroacetyl, trichloroethoxycarbonyl, 2,4-dimethoxybenzyloxycarbonyl, methoxymethyl, methylthiomethyl, methoxyethoxymethyl, [2-(trimethylsilyl)-ethoxy]-methyl, 2-(methylthiomethoxy)ethoxycarbonyl, tetrahydropyranyl or benzoyl, $R^3$ represents 3,4-dimethoxyphenyl, represents chlorine, bromine, cyano, cyanato, azido, $CF_3$, represents —$COR^{18}$, —$CONR^{19}R^{18}$, allyloxycarbonyl, 4-nitrobenzyloxycarbonyl, —$NHR^{18}$, ureido, guanidino, amidino, —$NHSO_2R^{20}$, —$OSO_2R^{20}$, —$OPO(OR^{19})$ $OR^{18}$, —S—$R^{18}$, —$SCOR^{18}$, —$SO_2OR^{18}$, —$SO_2NHR^{18}$, —SCN, —$SO_2R^{20}$, —S—$CONH_2$, —S—pyridyl, —S—pyrimidyl, —S—methyltetrazolyl, —S—thiadiazolyl, 2-aminothiadiazolyl or

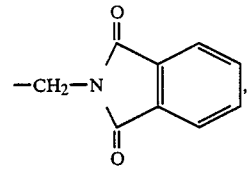

$R^{18}$ and $R^{19}$ being identical or different and representing hydrogen, representing straight-chain or branched alkyl (up to C$_6$), representing phenyl, 4-methylphenyl or benzyl, or representing a protective group for hydroxyl, mercapto or amino, and $R^{20}$ having the same meaning as $R^{19}$ and $R^{18}$ but not representing hydrogen or a protective group, and $R^4$ represents hydrogen or represents methyl, ethyl, tert.-butyl, decyl, 2-chloroethyl, 2,2,2-trichloroethyl, cyanoethyl, diphenylmethyl or triphenylmethyl, acetonyl, allyl, benzyl, 4-methoxybenzyl, 2,4-dimethoxybenzyl, tert.-butyldimethylsilyl, 1-phenoxyethyl or 2-methyl-2-propenyl, 4-nitrobenzyl, 2-nitrobenzyl, trimethylsilylethyl or dimethyltert.-butylsilylethyl or represents a radical of the formula

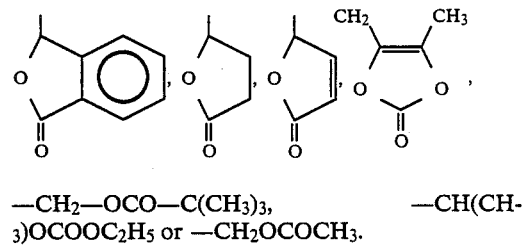

—$CH_2$—OCO—C(CH$_3$)$_3$, —CH(CH$_3$)OCOOC$_2$H$_5$ or —CH$_2$OCOCH$_3$.

2. A compound according to claim 1, in which $R^2$ represents hydrogen, chlorine, bromine, azido, $NHR^1$, a radical of the formula

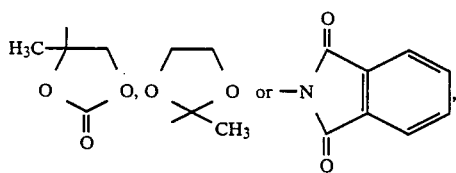

methyl, ethyl, i-propyl, tert.-butyl,

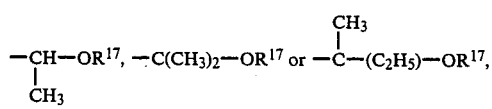

$R^{17}$ representing hydrogen, trimethylsilyl, tert.-butyl-dimethylsilyl, benzyloxycarbonyl, 4-nitrobenzyloxycarbonyl, tert.-butoxycarbonyl, allyloxycarbonyl or formyl or acetyl.

3. The compound 3-(tert.-butyldimethylsilyloxyethyl)-4-(3-allyoxycarbonyl-)-3-diazo-2-oxo-1-phenyl-propyl)-azetidin-2-one of the formula

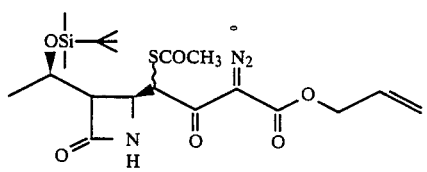

4. A compound according to claim 1 wherein such compound is 3-(1-tert.-butyldimethylsilyloxyethyl)-4-(1-acetylthio-3-allyloxycarbonyl-3-diazo-2-oxopropyl)-azetidin-2-one of the formula

* * * * *

UNITED STATES PATENT AND TRADEMARK OFFICE
CERTIFICATE OF CORRECTION

PATENT NO. : 4,841,042

DATED : June 20, 1989

INVENTOR(S) : Dieter Häbich, et al

It is certified that error appears in the above-identified patent and that said Letters Patent is hereby corrected as shown below:

| | |
|---|---|
| Col. 5, line 51 | Before formula insert --(b)-- |
| Col. 9, line 22 | Correct spelling of --nitrobenzyloxycarbonyl-- |
| Col. 11, line 63 | Before formula delete "or" |
| Col. 12, line 1 | Before formula insert --or-- |
| Col. 13, under "$R^3$", line 11 | Delete "CHNOH-" and substitute --CHONH-- |
| Col. 17, under "$R^3$", line 17 | Middle of formula delete "$\overset{O}{\underset{\|}{C}}$" and substitute --$\overset{NH}{\underset{\|}{C}}$-- |
| Col. 25, line 14 | Beginning of line, after "2H," delete "$\underline{CH}=CH_2$" and substitute --$CH-\underline{CH_2}$-- |
| Col. 33, Prep. Ex. No. 32, 6th column, line 1 | Delete "2145" and substitute --2135-- |
| Col. 33, Prep. Ex. No. 32, 8th column, line 1 | Delete "277.29" and substitute --277.2-- |
| Col. 39, line 4 | After "H-3β" insert --)-- |
| Col. 39, line 27 | Correct spelling of --oxobutanoate-- |
| Col. 39, line 48 | Beginning of line delete "(3s," and substitute --(3S,-- |
| Col. 41, line 15 | Delete "ally" and substitute --allyl-- |
| Col. 42, line 11 | Delete "lactame" and substitute --lactam-- |
| Col. 42, line 51 | Delete "$CH_3c-$" and substitute --$CH_3C-$-- |
| Col. 43, line 53 | After "4-[3-" insert --diazo-3- -- |
| Col. 44, line 55 | Top of formula correct --OSi-- |
| Col. 45, line 9 | End of line before "1H" insert --18 Hz,-- |

UNITED STATES PATENT AND TRADEMARK OFFICE
CERTIFICATE OF CORRECTION

PATENT NO. : 4,841,042
DATED : June 20, 1989
INVENTOR(S) : Dieter Häbich, et al

It is certified that error appears in the above-identified patent and that said Letters Patent is hereby corrected as shown below:

| | |
|---|---|
| Col. 49, Ex. 22, 7th column, line 6 | Delete "4.43" and substitute --4.34-- |
| Col. 50, Ex. No. 24, 7th column, line 10 | Line after "5.25-" delete number before "-6.05" and substitute --5.85--; next line delete "75.92" and substitute --5.92-- |
| Col. 53, line 13 | Bottom of formula delete "-CH$_3$" and substitute -- -CH$_2$-- |
| Col. 53, line 32 | After "J=2 Hz," insert --5 Hz,-- |

Signed and Sealed this

Eleventh Day of May, 1993

MICHAEL K. KIRK

Attest:

Attesting Officer

Acting Commissioner of Patents and Trademarks